US011046632B2

(12) United States Patent
Vautravers et al.

(10) Patent No.: US 11,046,632 B2
(45) Date of Patent: Jun. 29, 2021

(54) PROCESS FOR THE PREPARATION OF 3-METHYL-2-BUTEN-1-AL

(71) Applicant: BASF SE, Ludwigshafen am Rhein (DE)

(72) Inventors: Nicolas Vautravers, Ludwigshafen am Rhein (DE); Michaela Fenyn, Ludwigshafen am Rhein (DE); Joseph John Zakzeski, Ludwigshafen am Rhein (DE); Joaquim Henrique Teles, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/956,957

(22) PCT Filed: Dec. 5, 2018

(86) PCT No.: PCT/EP2018/083622
§ 371 (c)(1),
(2) Date: Jun. 22, 2020

(87) PCT Pub. No.: WO2019/121011
PCT Pub. Date: Jun. 27, 2019

(65) Prior Publication Data
US 2020/0339497 A1 Oct. 29, 2020

(30) Foreign Application Priority Data

Dec. 21, 2017 (EP) .................................. 17209513
Sep. 7, 2018 (EP) .................................. 18193181

(51) Int. Cl.
| C07C 45/29 | (2006.01) |
| C07C 45/38 | (2006.01) |
| B01J 23/42 | (2006.01) |
| B01J 21/18 | (2006.01) |
| C07C 47/21 | (2006.01) |

(52) U.S. Cl.
CPC ............. C07C 45/294 (2013.01); B01J 23/42 (2013.01); C07C 45/38 (2013.01); B01J 21/18 (2013.01); C07C 47/21 (2013.01)

(58) Field of Classification Search
CPC .............................. C07C 45/29; C07C 45/294
See application file for complete search history.

(56) References Cited

U.S. PATENT DOCUMENTS 6,013,843 A * 1/2000 Aquila ............... B01J 8/0242
568/450
6,476,260 B1 * 11/2002 Herrmann ............ B01J 23/644
562/534

FOREIGN PATENT DOCUMENTS

| EP | 0881206 A1 | 12/1998 | |
| FR | 2386509 A1 * | 11/1978 | ............. C07C 45/38 |
| WO | WO-2008037693 A1 | 4/2008 | |
| WO | WO-2018073367 A1 | 4/2018 | |

OTHER PUBLICATIONS

Schuster et al. Bacterial Degradation of tert-Amyl Alcohol Proceeds via Hemiterpene 2-methyl-3-buten-2-ol by Employing he Tertiary Alcohol Desaturase Function of the Rieske Nonheme Mononuclear Iron Oxygenase MdpJ. Journal of Baceteriology, vol. 194 (5), 972-981. (Year: 2012).*
Che, et al., "Chapter 2.: Preparation of Solid Catalysts, 2.2.1.1: Impregnation and Ion Exchange", Handbook of Heterogeneous Catalysis, ed. ERTL, et al., vol. 1, Jul 10, 1997, pp. 191-207.
Chen, et al., "A Surfactant-Free Strategy for Synthesizing and Processing Intermetallic Platinum-Based Nanoparticle Catalysts", Journal of the American Chemical Society, vol. 134, Issue 44, Oct. 11, 2012, pp. 18453-18459.
Cui, et al., "Synthesis of Structurally Ordered Pt3Ti and Pt3V Nanoparticles as Methanol Oxidation Catalysts", Journal of the American Chemical Society, vol. 136, Issue 29, Jul. 7, 2014, pp. 10206-10209.
Furukawa, et al., "Preparation of alumina-supported intermetallic compounds", RSC Advances, vol. 3, Issue 45, Oct. 2, 2013, pp. 23269-23277.
Huang, et al., "Sustainable catalytic oxidation of alcohols over the interface between air and water", Green Chemistry, vol. 17, Issue 4, Feb. 5, 2015, pp. 2325-2329.
Liu, et al., "Yolk-Shell Hybrid Materials with a Periodic Mesoporous Organosilica Shell: Ideal Nanoreactors for Selective Alcohol Oxidation", Advanced Functional Materials, vol. 22, Issue 3, Feb. 8, 2011, pp. 591-599.
Tonucci, et al., "Catalytic aerobic oxidation of allylic alcohols to carbonyl compounds under mild conditions", Green Chemistry, vol. 11, Issue 6, Mar. 11, 2009, pp. 816-820.
Zhang, et al., "High activity of PtBi intermetallics supported on mesoporous carbon towards HCOOH electro-oxidation", Electrochemistry Communications, vol. 25, Nov. 2012, pp. 105-108.
Zhang, et al., "One-Step, Facile and Ultrafast Synthesis of Phase- and Size-Controlled Pt-Bi Intermetallic Nanocatalysts through Continuous-Flow Microfluidics", Journal of the American Chemical Society, vol. 137, Issue 19, May 1, 2015, pp. 6263-6269.
Derdar, F. et al., "Cetonisation catalytique du methyl-2-butene-3-ol-2 par des complexes du rhodium(III) ou du palladium(II)", Journal of Organometallic Chemistry, vol. 338, No. 2, (1988), pp. C21-C26.
International Search Report for PCT/EP2018/083622 dated Jan. 7, 2019.

(Continued)

*Primary Examiner* — Sikarl A Witherspoon
(74) *Attorney, Agent, or Firm* — Faegre Drinker Biddle & Reath LLP (57) ABSTRACT

Process for the preparation of 3-methyl-2-buten-1-al, wherein 2-methyl-3-buten-2-ol is reacted to 3-methyl-2-buten-1-al in the presence of a catalyst, wherein the catalyst comprises a catalytically active metal and wherein the reaction is conducted at a pH of ≤7.

17 Claims, 1 Drawing Sheet

(56) References Cited

OTHER PUBLICATIONS

Lorber, C. et al., "Catalyzed oxidation of alcohols by cis-dioxomolybdenum(VI) complexes via oxygen atom transfer from sulfoxidest", Bulletin de la Societe Chimique de France, Societe Francasie de Chimie, vol. 133, (1996), pp. 755-758.

Ma, Z., et al., "Palladium nanoparticles confined in the nanocages of SBA-16: Enhanced recyclability for the aerobic oxidation of alcohols in water", Journal of Molecular Catalysis a: Chemical, vol. 331, Nos. 1-2, (2010), pp. 78-85.

Written Opinion of the International Searching Authority for PCT/EP2018/083622 dated Jan. 7, 2019.

\* cited by examiner

Figure 1

BSE

Figure 2

PROCESS FOR THE PREPARATION OF 3-METHYL-2-BUTEN-1-AL

CROSS-REFERENCE TO RELATED APPLICATIONS

This application is a national stage application (under 35 U.S.C. § 371) of PCT/EP2018/083622, filed Dec. 5, 2018, which claims benefit of European Application Nos. 18193181.7, filed Sep. 7, 2018, and 17209513.5, filed Dec. 21, 2017, all of which are incorporated herein by reference in their entirety.

The present invention relates to a process for the preparation of 3-methyl-2-buten-1-al by reacting 2-methyl-3-buten-2-ol in the presence of an oxidant and a catalyst, wherein the catalyst comprises a catalytically active metal and wherein the reaction is conducted at a pH of 7.

TECHNICAL BACKGROUND 3-methyl-2-buten-1-al ("prenal") is an important chemical intermediate especially for the preparation of terpene-based fragrances, such as citral, and for the preparation of vitamins, such as vitamin E, and therefore is of great technical and economic importance.

The most common procedures for preparing prenal use prenol (3-methyl-2-buten-1-ol) or isoprenol (3-methyl-3-buten-1-ol) as starting compounds. Thus, EP 0 881 206 describes the oxidation of these starting compounds with oxygen in the gas phase using a silver catalyst. The selectivity of this approach could be improved by further developing the catalytic system, as disclosed e.g. in WO 2008/037693. However, in order to obtain sufficient conversion rates and selectivity it is necessary to carry out the procedure in the gas phase at temperatures of about 360° C. while maintaining short contact times. This is required, on the one hand, to ensure adequate reactivity and, on the other hand, to prevent decomposition reactions of the sensitive reactants and products. These conditions can only be accomplished by using expensive equipment.

The oxidation of prenol to prenal in an aqueous liquid phase is described in Green Chem. 2015, 17, 2325-2329; Green Chem. 2009, 11, 816-820; Adv. Funct. Mater. 2012, 22, 591-599 as well as in Molecular Catalysis A: Chemical 2010, 331 (1-2). Prenol (3-methyl-2-buten-1-ol) is available only via isomerisation from isoprenol (3-methyl-3-buten-1-ol), which itself is available on a largescale only via an energy consuming high-pressure reaction of isobutene and formaldehyde.

It was an objective of the invention to provide a simple and efficient process for preparing 3-methyl-2-buten-1-al which is suitable for industrial scale preparations. The process should be easy to handle, provide high yields and high selectivity of 3-methyl-2-buten-1-al, thus avoiding over-oxidation to the corresponding acid. Moreover, the use of toxic or expensive reagents should be avoided. Moreover, the process should allow high space-time-yields (STY), which are of major importance for the economic suitability in industrial scale processes. The space-time-yield (STY) is defined as the amount of product obtained per reaction volume per hour of reaction, expressed as g/i/h. The reaction volume is the volume of the reactor in which the reaction takes place. In case the reaction is conducted in a cylindrical reactor, the reaction volume is the volume of the cylindrical reactor in which the reaction takes place. Of special interest are processes which allow high space-time-yields in a reaction time, in which at least 40%, preferably at least 50% conversion is achieved. Furthermore, it was desired to provide a process which enables easy recovery of the aldehyde.

Moreover, the process should allow a high specific activity (SA), which is of major importance for the economic suitability in industrial scale processes. The specific activity (SA) is defined as the amount of product obtained per amount of catalytically active metal per hour of reaction, expressed as g/g/h. Of special interest are processes which allow high specific activities in a reaction time, in which at least 40%, preferably at least 50% conversion is achieved.

SUMMARY OF THE INVENTION

It has now been found that the objectives are achieved by a process, wherein 2-methyl-3-buten-2-ol is reacted to 3-methyl-2-buten-1-al in the presence of an oxidant and a catalyst, wherein the catalyst comprises a catalytically active metal and wherein the reaction is conducted at a pH of 7.

It has surprisingly been found that 3-methyl-2-buten-1-al can be obtained with excellent yield and selectivity with the process according to the invention. The process according to the invention is further associated with a series of advantages. The process according to the invention enables the preparation of 3-methyl-2-buten-1-al with high yield and high selectivity under mild conditions, both of temperature and pressure, while requiring only moderate to low amounts of catalyst. The process can be performed with oxidants. The process can be conducted with no or low amounts of organic solvent, thus avoiding or minimizing environmentally problematic waste streams. The process also allows a simple isolation of the 3-methyl-2-buten-1-al. A further advantage of the process of the invention is that 3-methyl-2-buten-1-al is obtained in a high concentration in the reaction mixture, thus minimizing down-stream isolation steps.

Therefore, the present invention relates to a process for the preparation of 3-methyl-2-buten-1-al, wherein 2-methyl-3-buten-2-ol is reacted to 3-methyl-2-buten-1-al in the presence of an oxidant and a catalyst, wherein the catalyst comprises a catalytically active metal and wherein the reaction is conducted at a pH of ≤7.

Without wishing to be bound by this theory, it is assumed that 2-methyl-3-buten-2-ol is isomerized to 3-methyl-2-buten-1-ol, which is subsequently oxidized to 3-methyl-2-buten-1-al.

A BRIEF DESCRIPTION OF THE FIGURES

In FIG. 2 the Y-axis shows the local Pt-concentration in weight % measured by EDX, while the X-axis shows the position at which the measurement was taken. The distances are taken along the dotted line in the upper picture and the zero point is at the left side.

GENERAL DEFINITIONS

In the context of the present invention, the terms used generically are, unless otherwise stated, defined as follows:

Selectivity is defined as the number of moles of 3-methyl-2-buten-1-al formed divided by the number of moles of 2-methyl-3-buten-2-ol and 3-methyl-2-buten-1-ol that were consumed. The amounts of 3-methyl-2-buten-1-al, 3-methyl-2-buten-1-ol and 2-methyl-3-buten-2-ol can easily be determined by a GC analysis as defined in the experimental section.

The terms "conducted" and "performed" are used synonymously.

EMBODIMENTS OF THE INVENTION

The remarks made below regarding preferred embodiments of the reaction conditions of the process, apply either taken alone or, more particularly, in any conceivable combination with one another.

2-methyl-3-buten-2-ol

Reactant of the process of the invention is 2-methyl-3-buten-2-ol (DMVC, dimethyl vinyl carbinol). The reactant can further comprise 3-methyl-2-buten-1-ol. In one embodiment of the invention, the reactant comprises 2-methyl-3-buten-2-ol and 3-methyl-2-buten-1-ol.

3-methyl-2-buten-1-al

Product of the process of the invention is 3-methyl-2-buten-1-al (prenal).

Reaction Conditions pH

The reaction according to the invention is conducted at a pH of equal to or below (≤) 7, preferably the reaction is conducted at a pH of below 7, preferably equal to or below (≤) 6.

The pH of the reaction can for example be adjusted by the addition of acid(s), such as for example organic and/or inorganic acids. The pH of the reaction can for example be adjusted by the addition of acid(s) in liquid form and/or by the addition of acid(s) in solid form. The term "acid(s)" encompasses one or more than one acid.

Examples for suitable acid(s) are formic acid, acetic acid, phosphoric acid, sulfuric acid, hydrochloric acid, benzoic acid, citric acid and the like. Preferably acid(s) are employed which have a $pK_a$ value (determined in water at 25° C.) of below 5, preferably of below 3, more preferably between 0 and 2.5.

The pH of the reaction can for example be adjusted by performing the process in the presence of a strongly acidic cation exchanger, such as for example strongly acidic cation exchangers comprising or having sulfonic acid groups.

Strongly acidic cation exchangers are in particular ion exchanger resins in the H(+) form. Suitable examples of such are:
- strongly acidic ion exchangers (such as e.g. Amberlyst, Amberlite, Dowex, Lewatit, Purolite, Serdolit), which are based on polystyrene, and which comprise copolymers of styrene and divinylbenzene as carrier matrix with sulfonic acid groups in the H(+) form,
- ion exchanger groups functionalized with sulfonic acid groups ($—SO_3H$).

The ion exchangers differ in the structure of their polymer backbones, and a distinction is made between gel-like and macroporous resins. The strongly acidic ion exchanger resins are generally regenerated with hydrochloric acid and/or sulfuric acid.

Nafion® is the Dupont name for perfluorinated polymeric ion exchanger resins. These are perfluorinated ion exchanger materials consisting of fluorocarbon base chains and perfluorinated side chains which comprise sulfonic acid groups. The resins are produced by a copolymerization of perfluorinated, terminally unsaturated and sulfonyl-fluoride-functionalized ethoxylates with perfluoroethene. Nafion® belongs to the gel-like ion exchanger resins. An example of such a perfluorinated polymeric ion exchanger resin which may be mentioned is Nafion® NR-50.

Suitable strongly acidic cation exchangers in the H(+) form are those in which the ion exchanger comprises a polymer backbone having sulfonic acid groups and is either gel-like or comprises macroporous resins. Furthermore, ion exchanger based on a polystyrene backbone with sulfonic acid groups or on a perfluorinated ion exchanger resin with sulfonic acid groups can be used.

The commercially available strongly acidic cation exchangers are known under the trade names Lewatit® (Lanxess), Purolite® (The Purolite Company), Dowex® (Dow Chemical Company), Amberlite® (Rohm and Haas Company), Amberlyst™ (Rohm and Haas Company).

Strongly acidic cation exchangers that may be used are, for example: Lewatit® K 1221, Lewatit® K 1461, Lewatit® K 2431, Lewatit® K 2620, Lewatit® K 2621, Lewatit® K 2629, Lewatit® K 2649, Amberlite® IR 120, Amberlyst™ 131, Amberlyst™ 15, Amberlyst™ 31, Amberlyst™ 35, Amberlyst™ 36, Amberlyst™ 39, Amberlyst™ 46, Amberlyst™ 70, Purolite® SGC650, Purolite® C100H, Purolite® C150H, Dowex® 50X8, Serdolit® red and Nafion® NR-50.

Liquid Phase

It has surprisingly been found that the process according to the invention can be performed in the presence of a liquid phase. The liquid phase consists of all components of the reaction which are liquid at 20° C. and a pressure of 1 bar.

Depending on the catalyst and oxidant used, the process according to the invention is conducted in a liquid phase (catalyst and oxidant are part of the liquid phase, homogenous catalyzed process) or at the interphase between liquid phase and the solid catalyst (heterogeneous catalyzed process). The term "in the presence of a liquid phase" encompasses the process in a liquid phase as well as the process at the interphase.

The liquid phase can consist of one or more, e.g. two or three distinct liquid phases. The number of liquid phases can be chosen by a person skilled in the art, dependent for example on the concentration of the reactant, water or on optional solvent(s).

The process according to the invention can be conducted in the presence of a liquid phase, which consists of one liquid phase (mono-phase system). The process according to the invention can be conducted in the presence of a liquid phase, which consists of more than one, e.g. two, three or more distinct liquid phases (multi-phase system).

All weight-% of the liquid phase referred to in the process according to the invention are based on the total weight of the liquid phase, determined at a temperature of 20° C. and a pressure of 1 bar.

In case the process is conducted as a heterogeneous catalyzed process, the solid catalyst is not liquid at a temperature of 20° C. and a pressure of 1 bar and is therefore by definition not included in the weight-% of the liquid phase. In case the process is conducted in the presence of a solid acid, such as for example a strongly acidic cation exchanger, the solid acid is not liquid at a temperature of 20° C. and a pressure of 1 bar and is therefore by definition not included in the weight-% of the liquid phase.

Water

Water can be present in the liquid phase. If water is present, it is generally present in an amount of more than 0.1 weight-%, preferably of more than 0.5 weight-% to 99.5 weight-% of the liquid phase.

The process according to the invention can be conducted in the presence of a liquid phase which consists of one liquid phase, wherein the liquid phase contains at least 0.5 weight-%, preferably at least 5 weight-%, preferably at least 10 weight-%, more preferably at least 20 weight-%, more preferably at least 25 weight-% of water, determined at a temperature of 20° C. and a pressure of 1 bar.

The process according to the invention can be conducted in the presence of a liquid phase which consists of more than one liquid phase, wherein at least one distinct liquid phase contains at least 0.5 weight-%, preferably at least 5 weight-%, preferably at least 10 weight-%, more preferably at least 20 weight-%, more preferably at least 25 weight-% of water, based on the total weight of this distinct liquid phase, determined at a temperature of 20° C. and a pressure of 1 bar.

The process according to the invention can be performed in the presence of a liquid phase, which consists of two or three distinct liquid phases, wherein each distinct liquid phase contains at least 0.5 weight-%, preferably at least 5 weight-%, preferably at least 10 weight-%, more preferably at least 20 weight-%, more preferably at least 25 weight-% of water, based on the total weight of this distinct liquid phase, determined at a temperature of 20° C. and a pressure of 1 bar.

In one embodiment of the invention each distinct liquid phase contains at least 0.5 weight-%, preferably at least 5 weight-%, preferably at least 10 weight-%, more preferably at least 20 weight %, more preferably at least 25 weight-% of water, based on the total weight of this distinct liquid phase. The weight-% of water are determined at a temperature of 20° C. and a pressure of 1 bar.

The following preferred ranges for the water content of a liquid phase apply for the at least one or each distinct liquid phase accordingly.

In one embodiment of the invention the process is performed in a liquid phase, which contains at least 30 weight-%, preferably at least 40 weight-%, more preferably at least 50 weight-% of water. In a further embodiment, the process can be performed in a liquid phase, which contains at least 60 weight-%, preferably at least 70 weight-%, more preferably at least 80 weight-%, more preferably at least 90 weight-%, more preferably at least 95 weight-% of water. According to one embodiment of the invention, the process can be performed in a liquid phase which contains 99.5 weight-% of water. All weight-% are based on the total weight of the liquid phase (or the at least one or each distinct liquid phase in case more than one liquid phase is present).

In one embodiment of the invention the process is performed in a liquid phase, which contains 50 to 99.9 weight-%, preferably 60 to 99.5 weight-%, preferably 70 to 99 weight-%, preferably 75 to 95 weight-% of water. All weight-% are based on the total weight of the liquid phase (or the at least one or each distinct liquid phase in case more than one liquid phase is present).

In further embodiments of the invention the process is performed in a liquid phase, which contains 0.1 weight-% to less than 25 weight-%, or 0.1 weight-% to less than 50 weight-%, or 0.5 weight % to less than 60 weight-%, or 1 weight-% to less than 70 weight-%, or 5 weight-% to less than 75 weight-%, or 5 weight-% to less than 99.5 weight-% of water. All weight-% are based on the total weight of the liquid phase (or the at least one or each distinct liquid phase in case more than one liquid phase is present).

Reactant and Product

The liquid phase will typically contain from 0.5 to 99.5 weight-%, preferably from 10 to 90 weight % of reactant and product.

The process according to the invention can be conducted in the presence of a liquid phase which consists of one liquid phase, wherein the liquid phase contains at least 0.5 weight-%, preferably at least 5 weight-%, preferably at least 10 weight-%, more preferably at least 20 weight-%, more preferably at least 25 weight-%, of reactant and product.

The process according to the invention can be conducted in the presence of a liquid phase which consists of more than one liquid phase, wherein at least one distinct liquid phase contains at least 0.5 weight-%, preferably at least 5 weight-%, preferably at least 10 weight-%, more preferably at least 20 weight-%, more preferably at least 25 weight-%, of reactant and product, based on the total weight of this distinct liquid phase.

The process according to the invention can be performed in the presence of a liquid phase, which consists of two or three distinct liquid phases, wherein each distinct liquid phase contains at least 0.5 weight-%, preferably at least 5 weight-%, preferably at least 10 weight-%, more preferably at least 20 weight-%, more preferably at least 25 weight-% of reactant and product, based on the total weight of this distinct liquid phase, determined at a temperature of 20° C. and a pressure of 1 bar.

In one embodiment of the invention each distinct liquid phase contains at least 0.5 weight-%, preferably at least 5 weight-%, preferably at least 10 weight-%, more preferably at least 20 weight %, more preferably at least 25 weight-% of reactant and product, based on the total weight of this distinct liquid phase. The weight-% of water are determined at a temperature of 20° C. and a pressure of 1 bar.

The following preferred ranges for the weight-% of reactant and product of a liquid phase apply for the liquid phase for mono-phase systems or for the at least one distinct liquid phase for multi-phase systems.

In one embodiment of the invention the liquid phase contains at least 30 weight-%, preferably at least 50 weight-%, preferably at least 60 weight-%, preferably at least 70 weight-%, preferably at least 75 weight-%, preferably at least 80 weight-%, preferably at least 85 weight-%, preferably at least 90 weight-%, preferably at least 95 weight-% of reactant and product, based on the total weight of the liquid phase for mono-phase systems or the at least one distinct liquid phase for multi-phase systems.

In one embodiment of the invention the process is performed in a liquid phase, which contains 50 to 99.9 weight-%, preferably 60 to 99.5 weight-%, preferably 70 to 99 weight-%, preferably 75 to 95 weight-% of reactant and product. All weight-% are based on the total weight of the liquid phase (or the at least one or each distinct liquid phase in case more than one liquid phase is present).

In further embodiments of the invention the process is performed in a liquid phase, which contains 0.1 weight-% to less than 25 weight-%, or 0.1 weight-% to less than 50 weight-%, or 0.5 weight % to less than 60 weight-%, or 1 weight-% to less than 70 weight-%, or 5 weight-% to less than 75 weight-%, or 5 weight-% to less than 99.5 weight-% of reactant and product. All weight-% are based on the total weight of the liquid phase (or the at least one or each distinct liquid phase in case more than one liquid phase is present).

Oxidant

The process according to the invention is performed in the presence of at least one oxidant. The term "oxidant" encompasses one or more than one oxidants.

Suitable oxidants can for example be selected from the group consisting of halogens, oxygen, oxyanions of chlorine, oxyanions of bromine, oxyanions of iodine, dialkyl peroxides, organic and inorganic peroxy acids, peresters, hydroperoxides and hydrogen peroxide.

Suitable halogens are by way of example fluorine or chlorine. Suitable oxyanions of chlorine are by way of example hypochlorites, chlorites, chlorates or perchlorates. Suitable oxyanions of bromine are by way of example hypobromites, bromites, bromates or perbromates. Suitable oxyanions of iodine are by way of example hypoiodites, iodites, iodates or periodates. Suitable dialkyl peroxides are by way of example diisopropyl peroxide or di(tert-butyl) peroxide. Suitable organic or inorganic peroxy acids are for example, meta-chloroperoxybenzoic acid or peracetic acid, peroxydisulfuric acid or peroxymonosulphuric acid. Suitable peresters are by way of example peracetates, such as tert-butyl peracetate or tert-butyl phenylperacetate. Suitable hydroperoxides are by way of example tert-butyl hydroperoxide, 1-phenylethyl hydroperoxide (ethylbenzene hydroperoxide), 2-hydroperoxypropan-2-ylbenzene (cumyl hydroperoxide), cyclohexyl hydroperoxide or 1-methyl-1-(4-methylphenyl)ethyl hydroperoxide (p-cymene hydroperoxide).

For the purpose of the present invention, the expressions "hypochlorites", "chlorites", "chlorates" or "perchlorates" relate to any salt containing the oxyanion $ClO^-$ (hypochlorite), $ClO_2^-$ (chlorite), $ClO_3^-$ (chlorate) or $ClO_4^-$ (perchlorate), respectively, e.g. the alkali or earth alkali metal salts thereof. For the purpose of the present invention, the expressions "hypobromites", "bromites", "bromates" or "perbromates" relate to any salt containing the oxyanion $BrO^-$ (hypobromite), $ClO_2^-$ (bromite), $ClO_3^-$ (bromate) or $ClO_4^-$ (perbromate), respectively, e.g. the alkali or earth alkali metal salts thereof. For the purpose of the present invention, the expressions "hypoiodites", "iodites", "iodates" or "periodates" relate to any salt containing the oxyanion $IO^-$ (hypoiodite), $IO_2^-$ (iodite), $IO_3^-$ (iodate) or $IO_4^-/IO_6^{5-}$ (periodate), respectively, e.g. the alkali or earth alkali metal salts thereof. Preferably, the oxidant is selected from the group consisting of hydroperoxides, hydrogen peroxide and oxygen.

In a preferred embodiment, the oxidant is selected from the group consisting of tert-butyl hydroperoxide, 1-phenylethyl hydroperoxide (ethylbenzene hydroperoxide), 2-hydroperoxypropan-2-ylbenzene (cumyl hydroperoxide), cyclohexyl hydroperoxide, 1-methyl-1-(4-methylphenyl) ethyl hydroperoxide (p-cymene hydroperoxide), hydrogen peroxide and oxygen.

The process according to the invention can be performed with oxygen and/or hydrogen peroxide as oxidant. Oxygen can be used undiluted or diluted. The oxygen can be diluted with other inert gases like $N_2$, Ar or $CO_2$, e.g. in the form of air. In a preferred embodiment of the invention oxygen is used undiluted. Hydrogen peroxide can be used as an aqueous solution.

In a preferred embodiment of the invention oxygen is used as oxidant.

Solvent(s)

The process according to the invention can be carried out in the presence of a liquid phase which essentially consists of reactant, product, water, acid(s) and oxidant(s).

The process according to the invention can be carried out as a heterogeneous catalysed process in the presence of a liquid phase which essentially consist of reactant, product, water, and oxidant(s). Depending on the acid(s) chosen, the acid(s) can be part of the liquid phase or can be part of the solid phase.

The process according to the invention can be carried out as a homogenous catalysed process in the presence of a liquid phase which essentially consist of reactant, product, water, acid(s), oxidant(s) and catalyst(s).

In these embodiments, the liquid phase contains no solvent.

The term "solvent" encompasses any component other than reactant, product, water, oxidant(s), catalyst(s) or acid(s) which is liquid at a temperature of 20° C. and a pressure of 1 bar and which is thus part of the liquid phase.

It is one of the advantages of the present invention, that the process can be performed in the presence of a liquid phase, which contains less than 75 weight-%, preferably less than 70 weight % solvent based on the total weight of the liquid phase.

In case a solvent is employed, a suitable solvent can be selected depending on the reactant, product, catalyst(s), oxidant(s), acid(s) and reaction conditions. The term "solvent" encompasses one or more than one solvents.

The following preferred ranges for the solvent content of a liquid phase apply for the liquid phase (for mono-phase systems) or for the at least one distinct liquid phase (for multi-phase systems).

In a preferred embodiment of the invention the process is performed in a liquid phase, which contains less than 70 weight-%, preferably less than 60 weight-%, preferably less than 50 weight %, preferably less than 40 weight-%, preferably less than 30 weight-%, more preferably less than 20 weight-%, more preferably less than 10 weight-% solvent based on the total weight of the liquid phase (for mono-phase systems) or the at least one distinct liquid phase (for multi-phase systems).

Advantageously the process according to the invention can be performed in the presence of a liquid phase, which contains less than 5 weight-% solvent based on the total weight of the liquid phase (for mono-phase systems) or the at least one distinct liquid phase (for multi-phase systems). In one embodiment of the invention the process is performed in the presence of a liquid phase which contains less than 3 weight-%, preferably less than 1 weight-% of solvent. In one embodiment of the invention the process is performed in the presence of a liquid phase which contains no solvent.

In case a solvent is employed, suitable solvents are for example protic or aprotic solvents.

In case a solvent is employed, it has been found to be advantageous to use an aprotic organic solvent.

In case a solvent is employed, solvents are preferred that have a boiling point above 50° C., for instance in the range of 50 to 200° C., in particular above 65° C., for instance in the range of 65 to 180° C., and specifically above 80° C., for instance in the range of 80 to 160° C.

Useful aprotic organic solvents here include, for example, aliphatic hydrocarbons, such as hexane, heptane, octane, nonane, decane and also petroleum ether, aromatic hydrocarbons, such as benzene, toluene, the xylenes and mesitylene, aliphatic $C_3$-$C_8$-ethers, such as 1,2-dimethoxyethane (DME), diethylene glycol dimethyl ether (diglyme), diethyl ether, dipropyl ether, methyl isobutyl ether, tert-butyl methyl ether and tert-butyl ethyl ether, dimethoxymethane, diethoxymethane, dimethylene glycol dimethyl ether, dimethylene glycol diethyl ether, trimethylene glycol dimethyl ether, trimethylene glycol diethyl ether, tetramethylene glycol dimethyl ether, cycloaliphatic hydrocarbons, such as cyclohexane and cycloheptane, alicyclic $C_3$-$C_6$-ethers, such as tetrahydrofuran (THF), tetrahydropyran, 2-methyltetrahydrofuran, 3-methyltetrahydrofuran, 1,3-dioxolane, and 1,4-dioxane, 1,3,5-trioxane, short-chain ketones, such as acetone, ethyl methyl ketone and isobutyl methyl ketone, $C_3$-$C_6$-esters such as methyl acetate, ethyl acetate, methyl propionate, dimethyloxalate, methoxyacetic acid methyl ester, ethylene carbonate, propylene carbonate, ethylene glycol diacetate and diethylene glycol diacetate, $C_3$-$C_6$-amides such as dimethylformamide (DMF) and dimethylacetamide and N-methylpyrrolidone (NMP), dimethyl sulfoxide (DMSO), $C_3$-$C_6$-nitriles such as acetonitrile, propionitrile or mixtures of these solvents with one another.

According to an embodiment of the present invention those of the aforementioned aprotic solvents are preferred that have a boiling point above 50° C., for instance in the range of 50 to 200° C., in particular above 65° C., for instance in the range of 65 to 180° C., and specifically above 80° C., for instance in the range of 80 to 160° C.

More preferably the solvent, if employed, is selected from the group consisting of 1,2-dimethoxyethane (DME), diethylene glycol dimethyl ether (diglyme), diethoxymethane, dimethylene glycol dimethyl ether, tri-methylene glycol dimethyl ether, tetramethylene glycol dimethyl ether, 1,3-dioxolane, 1,4-dioxane, 1,3,5-trioxane, dimethylacetamide, methyl acetate, dimethyloxalate, methoxyacetic acid methyl ester, ethylene carbonate, propylene carbonate, ethylene glycol diacetate and diethylene glycol diacetate, toluene, the xylenes, mesitylene, $C_7$-$C_{10}$-alkanes, such as octane or nonane, THF, 1,4-dioxane and mixtures thereof, and specifically selected from toluene, orthoxylene, meta-xylene, para-xylene and mesitylene.

In a preferred embodiment, the solvent, if employed, is selected from solvents which have a water solubility of greater 150 g/l at 20° C. In a preferred embodiment the solvent, if employed, is selected from solvents which have a vapour pressure of below 100 mbar at 20° C.

In a preferred embodiment the solvent, if employed, is selected from the group consisting of diethylene glycol dimethyl ether, triethylene glycol dimethylether and dimethylacetamide, polyoxymethylene dimethylether of general formula (III) $H_3C$—O—$(CH_2O)_n$—$CH_3$ wherein n=3 to 8, dimethyloxalate, methoxyacetic acid methyl ester, ethylene carbonate, propylene carbonate, ethylene glycol diacetate and diethylene glycol diacetate.

Catalyst

The process according to the invention can be performed as a heterogeneous catalyzed process or as a homogeneous catalyzed process.

In a preferred embodiment of the invention the process is conducted as a heterogeneous catalysed process. In such a heterogeneous catalyzed process the catalyst and reactant/product are in different phases, which are in contact with each other. The reactant/product are in the liquid phase, whereas the catalyst will be, at least partially in a solid phase. The reaction will take place at the interphase between liquid phase and solid phase.

The process according to the invention is carried out in the presence of a catalyst. The catalyst comprises at least one catalytically active metal. In the process according to the invention the catalytically active metal can be selected from the elements selected from the groups 8, 9, 10 and 11 of the periodic table (according to IUPAC nomenclature). The elements of group 8, 9, 10 and 11 of the periodic table comprise iron, cobalt, nickel, ruthenium, rhodium, palladium, osmium, iridium, platinum, copper, silver and gold.

In a preferred embodiment, the catalytically active metal is selected from elements from the groups 10 and 11 of the periodic table (according to IUPAC nomenclature).

In a preferred embodiment, the catalytically active metal is selected from elements selected from the group consisting of platinum, palladium and gold.

In a preferred embodiment of the invention the catalytically active metal is platinum.

The catalytically active metal can be used in any form, e.g. unsupported or on a support. The catalytically active metal can be used in an unsupported form, for example as a powder, a mesh, a sponge, a foam or a net. In a preferred embodiment, the catalytically active metal is on a support.

The catalyst can optionally comprise one or more so called promotors, which enhance the activity of the catalytically active metal. Examples for such promotors are bismuth (Bi), antimony (Sb), lead (Pb), cadmium (Cd), tin (Sn), tellurium (Te), cerium (Ce), selenium (Se) or thallium (Tl).

In a preferred embodiment, the catalyst comprises at least one promotor selected from the group consisting of bismuth (Bi), antimony (Sb), lead (Pb), cadmium (Cd), tin (Sn) and tellurium (Te). In a preferred embodiment, the catalyst comprises at least one promotor selected from the group consisting of bismuth (Bi), lead (Pb) and cadmium (Cd). In a preferred embodiment, the catalyst comprises bismuth (Bi).

The promotors can for example be employed as metals, nitrates, acetates, sulphates, citrates, oxides, hydroxides or chlorides and mixtures thereof.

In a preferred embodiment, the catalytically active metal is platinum and the promotor is bismuth.

In case a promotor is employed, suitable molar ratios of the catalytically active metal and the promotor are in the range from 1:0.01 to 1:10, preferably 1:0.67 to 1:5, preferably 1:0.5 to 1:3, more preferably from 1:0.1 to 1:2.

The promotors can for example be present on the support or can be added separately to the process.

The term "on a support" encompasses that the catalytically active metal and/or promotor can be located on the outer surface of a support and/or on the inner surface of a support. In most cases, the catalytically active metal and/or promotor will be located on the outer surface of a support and on the inner surface of a support.

In case the catalytically active metal is on a support, the catalyst comprises the catalytically active metal, the support and optionally promotors.

In one embodiment of the invention, the process is conducted as a batch process and the molar ratio of the catalytically active metal to the alcohol(s) of general formula (II) is in the range 0.0001:1 to 1:1, more preferably in the range 0.001:1 to 0.1:1 and even more preferably in the range 0.001:1 to 0.01:1.

In one embodiment of the invention, the process is conducted as a continuous process and the catalyst load (defined as total amount of alcohol of general formula (II)/total amount of catalytically active metal in the reactor/time unit) is in the range 0.01 to 100 g of alcohol(s) of general formula (II) per g of catalytically active metal per hour, more preferably in the range 0.1 to 20 g of alcohol(s) of general formula (II) per g of catalytically active metal per hour.

In one embodiment of the invention, the process is conducted as a continuous process and the catalyst load (defined as total amount of alcohol of general formula (II)/total amount of catalytically active metal in the reactor/time unit) is in the range 30 to 40000 g of alcohol(s) of general formula (II) per g of catalytically active metal per hour, more preferably in the range 1000 to 9000, more preferably in the range 1200 to 5000, preferably 1500 to 4000, preferably in the range of 1650 to 3500 g of alcohol(s) of general formula (II) per g of catalytically active metal per hour.

In case the catalytically active metal is on a support, the support can for example be a powder, a shaped body or a mesh, for example a mesh of iron-chromium-aluminium (FeCrAl), that was tempered in the presence of oxygen (commercially available under the trademark Kanthal®).

In a preferred embodiment of the invention the catalytically active metal is employed on a support. In a preferred embodiment, the catalytically active metal is employed on a support and the support is selected from the group consisting of powders and shaped bodies. In case a support in the form of a powder is employed, such powders usually have a particle size in the range of 1 to 200 µm, preferably 1 to 100 µm. The shaped bodies can for example be obtained by extrusion, pressing or tableting and can be of any shape such as for example strands, hollow strands, cylinders, tablets, rings, spherical particles, trilobes, stars or spheres. Typical dimensions of shaped bodies range from 0.5 mm to 250 mm.

In a preferred embodiment, the support has a diameter from 0.5 to 20 mm, preferably from 0.5 to 10 mm, more preferably from 0.7 to 5 mm, more preferably from 1 to 2.5 mm, preferably 1.5 to 2.0 mm.

In a preferred embodiment, the support is obtained by extrusion and is in the form of a strand or hollow strand. In one embodiment, a support is employed with strand diameters from 1 to 10 mm, preferably 1.5 to 5 mm. In one embodiment, a support is employed with strand lengths from 2 to 250 mm, preferably 2 to 100 mm, preferably 2 to 25 mm, more preferably 5 to 10 mm. In one embodiment, a support is employed with a strand diameter of 1 to 2 mm and strand lengths of 2 to 10 mm.

In a preferred embodiment, the catalytically active metal is employed on a support, wherein the support is selected from the group consisting of carbonaceous and oxidic materials.

Suitable support materials are for example carbonaceous or oxidic materials. A preferred carbonaceous support is activated carbon. The surface area of carbonaceous support materials preferably is at least 200 $m^2/g$, preferably at least 300 $m^2/g$. In case a carbonaceous support is used an activated carbon with a surface area of at least 300 $m^2/g$ is preferred. In a preferred embodiment, the catalytically active metal (preferably platinum) is employed on an activated carbon support, preferably with an activated carbon support with a surface area of at least 300 $m^2/g$.

In case an oxidic support is used, the oxides of the following elements can be used: Al, Si, Ce, Zr, Ti, V, Cr, Zn, Mg. The invention also encompasses the use of mixed oxides comprising two or more elements. In one embodiment of the invention mixed oxides are used as support selected from the group consisting of (Al/Si), (Mg/Si) and (Zn/Si) mixed oxides. In a preferred embodiment, an oxidic support is used, selected from the group consisting of aluminum oxide and silcium dioxide. Aluminium oxide can be employed in any phase, such as alpha aluminium oxide ($\alpha$-$Al_2O_3$), beta aluminium oxide ($\beta$-$Al_2O_3$), gamma aluminium oxide ($\gamma$-$Al_2O_3$), delta aluminium oxide ($\delta$-$Al_2O_3$), eta aluminium oxide ($\eta$-$Al_2O_3$), theta aluminium oxide ($\theta$-$Al_2O_3$), chi aluminium oxide ($\chi$-$Al_2O_3$), kappa aluminium oxide ($\kappa$-$Al_2O_3$) and mixtures thereof. The term beta aluminium oxide ($\beta$-$Al_2O_3$) describes the compound $Na_2O.11Al_2O_3$.

In a preferred embodiment, the oxidic support is selected from the group consisting of alpha aluminium oxide ($\alpha$-$Al_2O_3$), beta aluminium oxide ($\beta Al_2O_3$), gamma aluminium oxide ($\gamma$-$Al_2O_3$), delta aluminium oxide ($\delta$-$Al_2O_3$), and theta aluminium oxide ($\theta$-$Al_2O_3$).

In a preferred embodiment, the oxidic support is selected from the group consisting of alpha aluminium oxide ($\alpha$-$Al_2O_3$), beta aluminium oxide ($\beta Al_2O_3$) and gamma aluminium oxide ($\gamma$-$Al_2O_3$).

In one embodiment, the oxidic support is gamma aluminium oxide ($\gamma$-$Al_2O_3$).

Commercially available gamma aluminium oxide ($\gamma$-$Al_2O_3$), can be treated at temperatures from 500 to 700° C., preferably at temperatures from 550° C. to 600° C. to ensure that the complete $Al_2O_3$ is in the gamma-phase.

In one embodiment the oxidic supports can have a BET-surface area (BET, Brunnauer-EmmetTeller determined according to DIN 66131 by $N_2$ adsorption at 77 K) from 0.1 to 500 $m^2/g$. Preferably the oxidic supports have a BET-surface area of at least 0.1 $m^2/g$, preferably at least 1 $m^2/g$, preferably at least 10 $m^2/g$, more preferably of at least 30 $m^2/g$, more preferably of at least 50 $m^2/g$, more preferably of at least 75 $m^2/g$, preferably of at least 100 $m^2/g$, preferably of at least 150 $m^2/g$ especially preferred of at least 200 $m^2/g$.

In a further embodiment, the oxidic support has a BET-surface area of 1 $m^2/g$ to 50 $m^2/g$. In a further embodiment, the oxidic support has a BET-surface area of 10 $m^2/g$ to 300 $m^2/g$, preferably of 20 to 100 $m^2/g$. In a further embodiment, the oxidic support has a BET-surface area of 100 $m^2/g$ to 300 $m^2/g$, preferably 150 to 300 $m^2/g$.

In a preferred embodiment, the support is $Al_2O_3$ with a BET-surface area of 100 to 300 $m^2/g$.

In one embodiment, the catalyst comprises platinum on a support.

In one embodiment, the catalyst comprises platinum on a support, wherein the support is selected from carbonaceous and oxidic materials.

In one embodiment, the catalyst comprises platinum on a support, wherein the support is selected from carbonaceous and oxidic materials, and wherein the oxidic material is selected from the group consisting of oxides of the elements selected from the group consisting of Al, Ce, Zr, Ti, V, Cr, Zn and Mg.

In one embodiment, the catalyst comprises of platinum on a support, wherein the support is selected from carbonaceous materials and oxidic materials, and wherein the oxide is selected from the group consisting of oxides of the elements selected from the group consisting of Al, Ce, Zr and Ti.

In a preferred embodiment, the catalyst is selected from the group consisting of platinum on carbon (Pt/C) and platinum on aluminium oxide (Pt/$Al_2O_3$).

In a preferred embodiment, the catalyst comprises platinum on aluminium oxide, wherein the aluminium oxide is selected from the group consisting of alpha aluminium oxide ($\alpha$-$Al_2O_3$), beta aluminium oxide ($\beta$-$Al_2O_3$), gamma aluminium oxide ($\gamma$-$Al_2O_3$), delta aluminium oxide ($\beta Al_2O_3$), eta aluminium oxide ($\eta$-$Al_2O_3$), theta aluminium oxide ($\theta$-$Al_2O_3$), chi aluminium oxide ($\chi$-$Al_2O_3$) and kappa aluminium oxide ($\kappa$-$Al_2O_3$).

In case the catalytically active metal is on a support, the content of the catalytically active metal of the catalyst usually is in the range of 0.1 to 20 weight-%, preferably 0.1 to 15 weight-%, preferably in the range of 0.5 to 10 weight-%.

In case the catalytically active metal is employed on a support, the catalyst can be prepared for example by a deposition-reduction method, in which a metal compound is first deposited on a support and then reduced to the catalytically active metal. The reduction can be performed with any known method, for example in the gas phase or in the liquid phase.

In a preferred embodiment of the invention, the catalyst is obtainable by
a) providing a support
b) providing a metal compound
c) depositing the metal compound on the support d) optionally calcinating the so obtained catalyst precursor
e) reducing the catalyst precursor
f) optionally recovering the catalyst.

In a preferred embodiment of the invention, the catalyst is obtained by
a) providing a support
b) providing a metal compound
c) depositing the metal compound on the support
d) optionally calcinating the so obtained catalyst precursor
e) reducing the catalyst precursor
f) optionally recovering the catalyst.

Step a) Providing a Support

A suitable support is provided, for example by adding the support in form of a powder or a shaped body directly to a reactor vessel or by providing the support as a slurry (in case the support is in form of a powder).

Step b) Providing a Metal Compound

The metal compound is a precursor of the catalytically active metal. The catalytically active metal is obtained by reduction of the metal compound.

The metal compound can be employed as solution, for example as an aqueous solution of a water-soluble salt of the metal compound or as a non-aqueous solution. The metal compound can also be employed as a colloid in which the non-dissolved metal compound is dispersed in a liquid phase.

In a preferred embodiment, the metal compound is employed as a salt. Depending on the solubility of the salt, aqueous or non-aqueous solutions can be employed.

Suitable salts of the metal compound include nitrates, acetates, sulphates, citrates, oxides, hydroxides and chlorides and combinations thereof. Preferably water-soluble salts are used.

In a preferred embodiment, the metal compound is selected from the group consisting of platinum salts. Depending on the solubility of the platinum salt, aqueous or non-aqueous solutions of the platinum salt can be employed. Examples for suitable platinum salts are $H_2PtCl$, $PtCl_4$, $Pt(NH_3)_2(NO_3)_2$, $Pt(NO_2)_2(NH_3)_2/NH_4OH$, $Pt(NO_3)_2$, platinum hydroxides such as $Pt(OH)_2$, $Pt(OH)_4$, or $H_2Pt(OH)_6$, all of which can be stabilized in amines, for example in monoethanolamine, $PtO_2$, bis(2,4-pentanedionato)Platinum (II)=$Pt(C_5H_7O_2)_2$, $K_2PtCl_4$, $NaPtCl_4$, $(NH_4)_2PtCl_4$.

In a preferred embodiment, the platinum salt is selected from the group consisting of $H_2PtCl$, $Pt(NH_3)_2(NO_3)_2$, $Pt(NO_2)_2(NH_3)_2/NH_4OH$ and $Pt(NO_3)_2$.

Generally, the deposition step c) will be performed prior to the reduction step e). The invention also encompasses the embodiment that the catalytically active metal can be reduced in situ from a metal compound and then deposited on the support.

In case promotors are employed, they can for example be employed as promotor compounds, which are subsequently converted (by oxidation and/or reduction) to the promotors. The promotor compound can be employed as solution, for example as an aqueous solution of a water-soluble salt of the promotor compound or as a non-aqueous solution of the promotor compound. The promotor compound can also be employed as a colloid in which the non-dissolved promotor compound is dispersed in a liquid phase.

Suitable salts of the promotor compound include nitrates, acetates, sulphates, citrates, oxides, hydroxides and chlorides and combinations thereof. Preferably water-soluble salts are used.

In case promotor compounds are employed, they can be added to the metal compound. In this embodiment, the metal compound and the promotor compound are deposited together on the support. In an alternative embodiment, the metal compound and the promotor compound can be deposited separately on the support.

After the one or more deposition step(s), both promotor compound and metal compound are then converted to promotor and catalytically active metal.

In a preferred embodiment, the promotor compound is selected from the group consisting of Bi salts, Cd salts and Pb salts.

Step c) Deposition Step

The deposition of the metal compound on the support can be performed with any known method, for example by chemical or physical vapour deposition or by contacting and mixing the support with the metal compound (=immersion) or by spraying the metal compound on the support.

In a preferred embodiment, the deposition is performed by immersion and/or spraying.

In case the deposition is performed by immersion or by spraying, the metal compound can be employed as solution or as colloid or as a colloid which is generated in situ during the immersion or spraying. The deposition by immersion or spraying can be performed at a temperature of 1 to 100° C. The pH value at which the deposition step is performed can be chosen depending on the metal compound used. The deposition can be performed from 0.1 to 24 hours, usually from 0.5 to 2 hours. The deposition can be performed at different pressures, for example at pressures from 1 to 1000 mbar (atmospheric pressure), suitable pressures are for example 50 mbar, 70 mbar, 100 mbar, 250 mbar, 500 mbar or atmospheric pressure. The so obtained catalyst precursor can optionally be dried and/or calcined prior to the reduction step.

In case the deposition step is performed by immersion or by spraying, the volume of the solution or colloid of the metal compound is ideally chosen, so that at least 90%, preferably 100% of the pore volume of the support will be filled with the solution or colloid (so called "incipient-wetness" method). The concentration of the metal compound is ideally chosen so that, after deposition and reduction, a catalyst with the desired content of catalytically active metal is obtained.

The deposition step can be conducted in one step or in multiple, consecutive steps. The deposition step can also be performed as a combination of spraying and immersion.

The catalyst precursor can then be recovered by suitable separation means such as filtration and/or centrifugation. The catalyst precursor can then be washed with water, preferably until a conductivity of less than 400 μS/cm, preferably less than 200 μS/cm is obtained.

In one embodiment, a drying step and/or a calcination step d) can be performed subsequent to the deposition step c).

The calcination step d) can be performed in customary furnaces, for example in rotary furnaces, in chamber furnaces, in tunnel furnaces or in belt calciners.

The calcination step d) can be performed at temperatures from above 200° C. to 1150° C., preferably from 250 to 900° C., preferably from 280° C. to 800° C. and more preferably from 500 to 800° C., preferably from 300° C. to 700° C. The calcination is suitably conducted for 0.5 to 20 hours, preferably from 0.5 to 10 hours, preferably from 0.5 to 5 hours.

The calcination of the catalyst precursor in step d) mainly serves the purpose to stabilize the metal compound (and if present also the promotor compound) deposited on the support and to remove undesired components.

Step e) Reduction Step

The so obtained catalyst precursor can then be reduced, for example by treatment with a gas (gas phase reduction) or by treatment of the catalyst precursor with a solution of a reducing agent (liquid phase reduction).

The gas phase reduction of the catalyst precursor can be performed by treating the catalyst precursor with hydrogen and/or CO. The hydrogen and/or CO can further comprise at least one inert gas, such as for example helium, neon or argon, $N_2$, $CO_2$ and/or lower alkanes, such as methane, ethane, propane and/or butane. Preferably $N_2$ is employed as the inert gas. The gas phase reduction can be performed at temperatures from 30° C. to 200° C., preferably from 50° C. to 180° C., more preferably from 60 to 130° C. Usually the gas phase reduction is performed over a period from 1 to 24 hours, preferably 3 to 20 hours, more preferably 6 to 14 hours.

The liquid phase reduction of the catalyst precursor is performed by treating the catalyst precursor with a solution of a reducing agent. Suitable reducing agents are quaternary alkyl ammonium salts; formic acid; salts of formic acid, such as sodium formate, potassium formate, lithium formate or ammonium formate; citric acid; salts of citric acid such as sodium citrate, potassium citrate, lithium citrate, ammonium citrate; ascorbic acid; salts of ascorbic acid such as sodium ascorbate, potassium ascorbate, lithium ascorbate and ammonium ascorbate; tartaric acid; salts of tartaric acid, such as sodium tartrate, potassium tartrate, lithium tartrate and ammonium tartrate; oxalic acid; salt of oxalic acid, such as potassium oxalate, sodium oxalate, lithium oxalate and ammonium oxalate; ammonium hydrogen carbonate ($NH_4HCO_3$); hydroxylamine; hypophosphoric acid; hyposphosphites, such as for example sodium hypophosphite ($NaH_2PO_2$); sodium sulfite ($Na_2SO_3$); hydrazine; phenylhydrazine; $C_1$ to $C_4$ alcohols such methanol, ethanol, 1-propanol, 2-propanol, 1-butanol, iso-butanol (2-methyl-1-propanol), 2-butanol; diols; polyols; reducing sugars, such as glucose, fructose; borohydrides, such as $LiBH_4$, $NaBH_4$, $NaBH_3CN$, $KBH_4$, $KBH(C_2H_5)_3$, $LiBH(C_2H_5)_3$; diboran ($B_2He$); lithium aluminium hydride ($LiAlH_4$); formaldehyde; N-vinyl pyrrolidone (NVP), polyvinyl-pyrrolidone (PVP); phenol; sodium thiocyanate; iron(II) sulfate; sodium amalgam; zinc mercury amalgam.

The liquid phase reduction can be performed at a temperature from 10 to 95° C., preferably from 50 to 90° C. The pH of the reduction step can be chosen depending on the reducing agent used.

In a preferred embodiment, the reduction step is performed by treatment of the catalyst precursor with a solution of a reducing agent.

In a preferred embodiment, the reduction step is performed by treatment of the catalyst precursor with a solution of a reducing agent, wherein the reducing agent is selected from the group consisting of quaternary alkyl ammonium salts; formic acid; salts of formic acid, such as sodium formate, potassium formate, lithium formate or ammonium formate; citric acid; salts of citric acid such as sodium citrate, potassium citrate, lithium citrate, ammonium citrate; ascorbic acid; salts of ascorbic acid such as sodium ascorbate, potassium ascorbate, lithium ascorbate and ammonium ascorbate; tartaric acid; salts of tartaric acid, such as sodium tartrate, potassium tartrate, lithium tartrate and ammonium tartrate; oxalic acid; salt of oxalic acid, such as potassium oxalate, sodium oxalate, lithium oxalate and ammonium oxalate; ammonium hydrogen carbonate ($NH_4HCO_3$); hydroxylamine; hypophosphoric acid; hypophosphites, such as for example sodium hypophosphite ($NaH_2PO_2$); sodium sulfite ($Na_2SO_3$); hydrazine; phenylhydrazine; $C_1$ to $C_4$ alcohols such methanol, ethanol, 1-propanol, 2-propanol, 1-butanol, iso-butanol (2-methyl-1-propanol), 2-butanol; diols; polyols; reducing sugars, such as glucose, fructose; borohydrides, such as $LiBH_4$, $NaBH_4$, $NaBH_3CN$, $KBH_4$, $KBH(C_2H_5)_3$, $LiBH(C_2H_5)_3$; diboran ($B_2He$); lithium aluminium hydride ($LiAlH_4$); formaldehyde; N-vinyl pyrrolidone (NVP), polyvinyl-pyrrolidone (PVP); phenol; sodium thiocyanate; iron(II) sulfate; sodium amalgam; zinc mercury amalgam.

In a preferred embodiment, the reduction step is performed by treatment of the catalyst precursor with a solution of a reducing agent, wherein the reducing agent is selected from the group consisting of sodium formate, sodium citrate, sodium ascorbate, polyols, reducing sugars, formaldehyde, methanol, ethanol, 2-propanol, $KBH(C_2H_5)_3$ and $LiBH(C_2H_5)_3$.

The catalyst can then be recovered by suitable separation means such as filtration and/or centrifugation. Typically, the catalyst is then washed with water, preferably until a conductivity of less than 400 µS/cm, preferably less than 200 µS/cm is obtained.

Drying steps can be performed for example subsequent to step c) and/or subsequent to step e). The drying of the catalyst precursor obtained in step c) or of the catalyst obtained in step e) can generally be performed at temperatures above 60° C., preferably above 80° C., more preferably above 100° C. The drying can for example be performed at temperatures from 120° C. up to 200° C. The drying will normally be performed until substantially all the water is evaporated. Common drying times range from one to up to 30 hours and depend on the drying temperature. The drying step can be accelerated by the use of vacuum.

In one embodiment of the invention the catalyst comprises at least one catalytically active metal and at least one promotor.

The catalyst can comprise the at least one catalytically active metal and the at least one promotor in any structure, for example unstructured (random distribution of catalytically active metal and promotor) or in an ordered or partially ordered structure [=as an intermetallic compound (IMC)] as well as in varying shares of these states.

In one embodiment of the invention at least 50 wt.-%, at least 60 wt.-%, at least 70 wt.-%, preferably the at least 85 wt.-%, preferably at least 90 wt.-% and more preferably at least 95 wt.-% of the at least one catalytically active metal and the at least one promotor are in the structure of an intermetallic compound.

In one embodiment of the invention the catalyst comprises the at least one catalytically active metal A and the at least one promotor B as an intermetallic compound of the general formula $A_xB_y$, wherein x in $A_xB_y$ is in the range 0.05-10, preferably from 0.1 to 5, preferably from 0.2 to 4, more preferably 0.25 to 3, more preferably from 0.5 to 2, more preferably from 0.67 to 1.

y in $A_xB_y$ is in the range 0.05-10, preferably from 0.1 to 5, preferably from 0.2 to 4, more preferably 0.25 to 3, more preferably from 0.5 to 2, more preferably from 0.67 to 1.

In one embodiment of the invention the catalyst comprises the at least one catalytically active metal A and the at least one promotor B as an intermetallic compound of the general formula $A_xB_y$, wherein A is one or more elements selected from Fe, Co, Ni, Ru, Rh, Pd, Os, Ir, Pt, Cu, Ag and Au, B is one or more elements selected from Bi, Sb, Pb, Cd, Sn, Te, Ce, Se and Tl x in $A_xB_y$ is in the range 0.05-10, preferably from 0.1 to 5, preferably from 0.2 to 4, more preferably 0.25 to 3, more preferably from 0.5 to 2, more preferably from 0.67 to 1.

y in $A_xB_y$ is in the range 0.05-10, preferably from 0.1 to 5, preferably from 0.2 to 4, more preferably 0.25 to 3, more preferably from 0.5 to 2, more preferably from 0.67 to 1.

More preferred are intermetallic compounds of general formula $A_xB_y$, wherein
A is one or more elements selected from Pd, Pt and Au,
B is one or more elements selected from Bi, Pb and Cd,
x in $A_xB_y$ is in the range 0.05-10, preferably from 0.1 to 5, preferably from 0.2 to 4, more preferably 0.25 to 3, more preferably from 0.5 to 2, more preferably from 0.67 to 1.
y in $A_xB_y$ is in the range 0.05-10, preferably from 0.1 to 5, preferably from 0.2 to 4, more preferably 0.25 to 3, more preferably from 0.5 to 2, more preferably from 0.67 to 1.

Even more preferred are intermetallic compounds of the general formula $A_xB_y$, wherein
A is Pt,
B is one or more elements selected from Bi, Pb and Cd,
x in $A_xB_y$ is in the range 0.05-10, preferably from 0.1 to 5, preferably from 0.2 to 4, more preferably 0.25 to 3, more preferably from 0.5 to 2, more preferably from 0.67 to 1.
y in $A_xB_y$ is in the range 0.05-10, preferably from 0.1 to 5, preferably from 0.2 to 4, more preferably 0.25 to 3, more preferably from 0.5 to 2, more preferably from 0.67 to 1.

Even more preferred are intermetallic compounds of the general formula $A_xB_y$, wherein
A is Pt, B is Bi,
x in $A_xB_y$ is in the range 0.05-10, preferably from 0.1 to 5, preferably from 0.2 to 4, more preferably 0.25 to 3, more preferably from 0.5 to 2, more preferably from 0.67 to 1.
y in $A_xB_y$ is in the range 0.05-10, preferably from 0.1 to 5, preferably from 0.2 to 4, more preferably 0.25 to 3, more preferably from 0.5 to 2, more preferably from 0.67 to 1.

An intermetallic compound (IMC) in terms of this invention is a compound made from at least two different metals in an ordered or partially ordered structure with defined stoichiometry. The structure can be similar or different to the structure of the pure constituent metals. Examples for intermetallic compounds are ordered, partially ordered and eutectic alloys, Laves-phases, Zintlphases, Heussler-phases, Hume-Rothary-phases, and other intermetallic compounds known to the skilled in the art. Also included are compounds comprising elements belonging to the group of semimetals, like selenides, tellurides, arsenides, antimonides, silizides, germanides and borides.

The term intermetallic compound (IMC) also encompasses mixtures of different intermetallic compounds of general formula $A_xB_y$ as specified hereinbefore.

Examples for intermetallic compounds according to this invention are $RhPb$, $RhPb_2$, $Rh_4Pb_5$, $Rh_2Sn$, $RhSn$, $RhSn_2$, $RhSn_4$, $Rh_2Sb$, $RhSb$, $RhSb_2$, $RhSb_3$, $IrPb$, $IrSn$, $Ir_5Sn$, $IrSn_2$, $Ir_3Sn_2$, $IrSn_4$, $IrSn$, $Ir_5Sn$, $IrSn_2$, $Ir_3Sn_2$, $IrSn_4$, $Pd_3Pb$, $Pd_{13}Pb_5$, $Pd_5Pb_3$, $PdPb$, $Pd_3Sn$, $Pd_{20}Sn_{13}$, $Pd_2Sn$, $PdSn$, $Pd_5Sn$, $PdSn_2$, $PdSn_3$, $PdSn_4$, $Pd_3Sb$, $Pd_{20}Sb_7$, $Pd_5Sb_2$, $Pd_8Sb_3$, $Pd_2Sb$, $PdSb$, $PdSb_2$, $Ru_3Sn_3$, $RuSn_2$, $Ru_3Sn_7$, $RuSb$, $RuSb_2$, $RuSb_3$, $NiPb$, $Ni_3Sn_4$, $Ni_3Sn_2$, $Ni_3Sn$, $NiSn$, $Ni_5Sb_2$, $Ni_3Sb$, $NiSb_2$, $NiSb_3$, $PtBi$, $PtBi_2$, $Pt_2Bi_3$, $PtPb$, $Pt_3Pb$, $PtPb_2$, $PtPb_4$, $PtSb$, $PtSb_2$, $Pt_{0.3}Sb_{0.7}$, $Pt_3Sb$, $Pt_3Sb_2$, $PtSb$, $PtSn$, $Pt_{0.9}Sn_{0.1}$, $Pt_{0.94}Sn_{0.06}$, $PtSn_2$, $PtSn_4$, $Pt_2Sn_3$, and $Pt_3Sn$.

Preferred intermetallic compounds are selected from the group consisting of $PtBi$, $PtBi_2$, $Pt_2Bi_3$, $PtPb$, $Pt_3Pb$, $PtPb_2$, $PtPb_4$, $PtSb$, $PtSb_2$, $Pt_{0.3}Sb_{0.7}$, $Pt_3Sb$, $Pt_3Sb_2$, $PtSb$, $PtSn$, $Pt_{0.9}Sn_{0.1}$, $Pt_{0.94}Sn_{0.06}$, $PtSn_2$, $PtSn_4$, $Pt_2Sn_3$, and $Pt_3Sn$ Preferred intermetallic compounds are selected from the group consisting of $PtBi$, $PtBi_2$ and $Pt_2Bi_3$.

The presence of intermetallic compounds can be detected by standard methods for characterizing solids, like for example electron microscopy, solid state NMR, XPS (X-ray photoelectron spectroscopy) or Powder X-Ray Diffraction (PXRD). PXRD-analysis can preferably be employed for unsupported intermetallic compounds, whereas XPS analysis is preferred for the analysis of supported intermetallic compounds. PXRD-analysis can for example be performed as described in Zhang et al., J. Am. Chem. Soc. (2015) 137, p 6264 "Characterization of Pt—Bi intermetallic NPs" or as described in Cui et al., J Am. Chem. Soc. (2014), 136, 10206-10209 and the Supporting Information thereto. XPS can for example be performed as described in the examples below.

Preparation of IMCs

IMCs can be prepared by standard methods, for example as described in Zhang et al., J. Am. Chem. Soc. (2015) 137, 6263-6269; Zhang et. al., Electrochemistry Communications (2012) 25, 105-108 or Furukawa et al., RSC Adv. (2013), 3, 23269-23277. IMCs can also be prepared by the so called "DiSalvo" Method, as described in Cui et al., J. Am. Chem. Soc. (2014), 136.10206-10209 or Chen et al. (2012), J. Am. Chem. Soc. 134, 18453-18459. IMCs can also for example be prepared as described in WO 2018073367.

Step g) Preparation of IMCs

In one embodiment the intermetallic compounds (IMCs) are obtainable by
g-1) providing a composition comprising the at least one metal compound and the at least one promotor compound
g-2) reducing the composition
g-3) performing an annealing step
g-4) optionally recovering the IMCs.

It is within the scope of the invention, that IMCs are obtainable in a reaction, which combines steps g-1) and g-2) or steps g-2) and g-3).

Step g-1)

The metal compound and the promotor compound can be provided for example as described in step-b) above. In a preferred embodiment the metal compound and the promotor compound are provided in a solvent, preferably in an aprotic solvent as describe above.

In one embodiment of the invention, the metal compound and the promotor compound are provided as chlorides.

Step g-2)

The reducing of the composition is preferably performed as described in step e) above for the reduction of the catalyst precursor.

In case the reducing agent in step g-2) is provided in a solvent, it is preferred that the solvent is identical to the solvent of composition provided in step g-1).

It is within the scope of the invention to employ a stabilizer and/or a solvent which also serve(s) as a reducing agent.

In one embodiment of the invention the reducing agent is selected from the group consisting of potassium triethyl borohydride ($K(C_2H_5)_3BH$) and lithium triethyl borohydride ($Li(C_2H_5)_3BH$).

In one embodiment of the invention, step g-1) and step g-2) are performed in a one pot reaction.

In one embodiment of the invention, step g-1) and step g-2) are performed in a one pot reaction, the metal compound and the promotor compound are provided as chlorides and the reducing agent is selected from potassium triethyl borohydride (K(C$_2$H$_5$)$_3$BH) and lithium triethyl borohydride (Li(C$_2$H$_5$)$_3$BH). In this embodiment the generated insoluble by-product KCl or LiCl then serves as a matrix that stabilizes the IMCs generated and minimizes agglomeration. Typically, such a one pot reaction is performed in an aprotic solvent, for example in THF.

To control the size of the IMCs and/or to prevent agglomeration, a stabilizer, preferably an inorganic stabilizer can be added to the composition in step g-2) or a reducing agent, which also serves as stabilizer can be employed. Likewise, a solvent, which also serves as a stabilizer can be employed in step g-4 (for example ethylene glycol).

Step g-3) Annealing Step

The annealing step is preferably performed by treatment of the composition obtained in step g-2) at temperatures between 200 to 700° C.

In a further embodiment, steps g-2) and g-3) can be combined into a single step by thermal treatment of the composition obtained in step g-1) in the presence of a reducing agent or at a temperature where reduction occurs.

Step g-4) Recovering of IMCs

In one embodiment the IMCs can be employed directly as obtained after the annealing step. In an alternative embodiment the IMCs can be recovered, for example by suitable separation means such as filtration and/or centrifugation. The recovery step can preferably be performed in the presence of a stabilizer, such as for example PVP or ethylene glycol.

The so obtainable IMCs can be of various sizes, for example in the range of 1 to 50 nm, preferably 5 to 30 nm, but can also be in the size of μm (agglomerates). The size of the IMC can be adjusted by means known to a person skilled in the art, for example by choice of solvent and/or stabilizer and/or time of the annealing step. The structure of the IMCs is generally adjusted by varying the temperature of the annealing step.

The at least one catalytically active metal and the at least one promotor as an intermetallic compound (IMC) can be used in any form, e.g. unsupported or on a support.

In case the at least one catalytically active metal and the at least one promotor as an intermetallic compound (IMC) are on a support, the catalyst can for example be prepared by
providing a support as described in step a) above,
providing the IMC, preferably prepared as described in step g) above
depositing the IMC on the support as described in step c) above
optionally performing a drying step In one embodiment of the invention, the catalyst is obtainable by
providing a support
providing the at least one catalytically active metal and the at least one promotor as an intermetallic compound (IMC),
depositing the IMC on the support,
optionally performing a drying step In one embodiment of the invention, the catalyst is obtainable by
providing a support, preferably as described in step a) above,
providing the at least one catalytically active metal and the at least one promotor as an intermetallic compound (IMC), preferably prepared as described in step g) above)
depositing the IMC on the support, preferably as described in step c) above
optionally performing a drying step In case the at least one catalytically active metal and the at least one promotor as an intermetallic compound (IMC) are on a support, the catalyst can—in an alternative embodiment—be prepared by
(i) providing a support as described in step a) above
(ii) providing a composition comprising the at least one metal compound and the at least one promotor compound as described in step b) above
(iii) depositing the composition on a support as described in step c) above
(iiia) optionally performing a drying and/or calcination step
(iv) reducing the so obtained catalyst precursor as described in step e) above and
(v) performing an annealing step, preferably at temperatures of 200 to 700° C.

In one embodiment of the invention, the catalyst is obtainable by
(i) providing a support
(ii) providing a composition comprising the at least one metal compound and the at least one promotor compound
(iii) depositing the composition on a support
(iiia) optionally performing a drying and/or calcination step
(iv) reducing the so obtained catalyst precursor and
(v) performing an annealing step.

In one embodiment of the invention, the catalyst is obtainable by
(i) providing a support, preferably as described in step a) above
(ii) providing a composition comprising the at least one metal compound and the at least one promotor compound, preferably as described in step b) above
(iii) depositing the composition on a support, preferably as described in step c) above
(iiia) optionally performing a drying and/or calcination step as described in step d) above
(iv) reducing the so obtained catalyst precursor, preferably as described in step e) above and
(v) performing an annealing step, preferably at temperatures of 200 to 700° C.

Annealing Step (v)

The annealing step is preferably performed by treatment of the catalyst obtained in step (iv) at temperatures between 200 to 700° C.

In a further embodiment, steps (iv) and (v) can be combined into a single step by thermal treatment of the precursor obtained in step (iii) in the presence of a reducing agent or at a temperature where reduction occurs.

Annealing Step g-3) or (v)

The annealing step is preferably performed at temperatures between 200 to 700° C., preferably under chemically inert conditions.

The annealing step is the step in which the IMC structure is mainly generated. The extend of the IMC structure can be adjusted for example by varying the temperature or the duration of the annealing step.

The extent to which the IMCs structure is obtained can be monitored for example by PXRD analysis. If needed, the temperature and/or time of thermal treatment can be adapted, to achieve the desired extend of IMC structure.

Generally, the annealing steps g-3) or (v) are performed by heating the composition obtained in step g-2) or the catalyst obtained in step (iii) to the desired temperature under chemically inert conditions wherein the gas mixture present does not contain any reactive components that can undergo chemical reaction with the composite material. Particularly the mixture should not comprise oxidizing agents like for example oxygen, water, $NO_x$, halides or there like. The heating can be performed by any method suited to heat solids or wet solids like heating in muffle furnaces, microwaves, rotary kilns, tube furnaces, fluidized bed and other heating devices known to the person skilled in the art.

Distribution on the Support

In case the catalytically active metal is employed on a support, the catalytically active metal can be evenly distributed on the support or can be unevenly distributed on the support. The catalytically active metal can for example be concentrated in the core or in defined layers of the support. The catalytically active metal can be located partially or completely on the inner surface of the support or can be located partially or completely on the outer surface of the support.

For all embodiments of the invention, in case the catalyst comprises a catalytically active material and a promotor, catalytically active material and promotor can be in any structure, for example unstructured or in an ordered or partially ordered structure [as an intermetallic compound (IMC)] as well as in varying shares of these states as described above.

In case the catalytically active metal is located completely on the inner surface of the support, the outer surface of the catalyst is identical to the outer surface of the support.

The distribution of the catalytically active metal can be determined with Scanning Electron Microscopy (SEM) and Energy Dispersive X-Ray Spectroscopy (EDXS). The distribution can for example be determined by preparing a cross section of the catalyst. In case the catalyst is a sphere the cross section can be prepared through the center of the sphere. In case the catalyst is a strand, the cross section can be prepared by cutting the strand at a right angle to the axis of the strand. Via backscattered electrons (BSE) the distribution of the catalytically active metal in the catalyst can be visualized. The amount of catalytically active metal can then be quantified via EDXS whereby an acceleration voltage of 20 kV is usually used.

In a preferred embodiment of the invention a catalyst is employed, wherein the catalytically active metal is located in the outer shell of the catalyst. In this embodiment, the catalytically active metal is mainly located in the outer shell of the catalyst.

In one embodiment, the outer shell of the catalyst is the space from the outer surface of the catalyst to a depth of X from the outer surface of the catalyst, wherein X is 15% of the distance from the outer surface of the catalyst to the center of the catalyst. For example, in case a catalyst is employed which is a sphere and has a diameter of 1.5 mm, the outer shell is the space from the outer surface to a depth of 112.5 µm from the outer surface.

In one embodiment, the outer shell of the catalyst is the space from the outer surface of the catalyst to a depth of X from the outer surface of the catalyst, wherein X is 30% of the distance from the outer surface of the catalyst to the center of the catalyst. For example, in case a catalyst is employed which is a sphere and has a diameter of 1.5 mm, the outer shell is the space from the outer surface to a depth of 225 µm from the outer surface.

In one embodiment, the outer shell of the catalyst is the space from the outer surface of the catalyst to a depth of 100 µm from the outer surface of the catalyst.

In one embodiment, the outer shell is the space from the outer surface of the catalyst to a depth of 400 µm, preferably 300 µm, preferably 200 µm from the outer surface of the catalyst.

In a preferred embodiment, at least 50 weight-%, preferably at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of X from the outer surface of the catalyst, wherein X is 15% of the distance from the outer surface of the catalyst to the center of the catalyst.

In a preferred embodiment, at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of X from the outer surface of the catalyst, wherein X is 30% of the distance from the outer surface of the catalyst to the center of the catalyst.

In a further embodiment of the invention, at least 50 weight-%, preferably at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of 100 µm from the outer surface of the catalyst.

In a further embodiment of the invention, at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of 400 µm, preferably to a depth of 300 µm, preferably to a depth of 200 µm from the outer surface of the catalyst.

In a further embodiment of the invention, a catalyst is employed, wherein the dispersity of the catalytically active metal is on average in the range of 10% to 100%, preferably 30% to 95% (determined with CO-sorption according to DIN 66136-3).

Catalysts in which the catalytically active metal is located in the outer shell of the catalyst can for example be obtained by the deposition-reduction method as described above. The distribution of the catalytically active metal in the outer shell of the catalyst can be effected for example by the choice of the deposition method and/or the choice of the deposition parameters such as temperature, pH and time and the combination of these parameters. A description of the different methods of preparation can for example be found in "Handbook of Heterogeneous Catalysis", edited by G. Ertl, H. Kndzinger, J. Weitkamp, Vol 1. Wiley-VCH, 1997. Chapter 2, part 2.2.1.1. Impregnation and Ion Exchange, authors M. Che, O. Clause, and Ch. Marcilly, p. 315-340.

The promotor can be evenly distributed on the support or can be unevenly distributed on the support. In a preferred embodiment, the promotor is distributed in the same way as the catalytically active material on the support.

One embodiment of the invention is directed to a process for the preparation of 3-methyl-2-buten-1-al, wherein 2-methyl-3-buten-2-ol is reacted to 3-methyl-2-buten-1-al in the presence of an oxidant and a catalyst, wherein the catalyst comprises a catalytically active metal, preferably selected from the group consisting of platinum, palladium and gold, and wherein the reaction is conducted at a pH of 7 and wherein a catalyst is used which is obtainable by a) providing a support
b) providing a metal compound
c) depositing the metal compound on the support
d) optionally calcinating the so obtained catalyst precursor
e) reducing the catalyst precursor, preferably by treatment of the catalyst precursor with a solution of a reducing agent,
f) optionally recovering the catalyst.

One embodiment of the invention is directed to a process for the preparation of 3-methyl-2-buten-1-al, wherein 2-methyl-3-buten-2-ol is reacted to 3-methyl-2-buten-1-al in the presence of an oxidant and a catalyst, wherein the catalyst comprises a catalytically active metal, preferably selected from the group consisting of platinum, palladium and gold, and wherein the reaction is conducted at a pH of 7 and wherein a catalyst is used which is obtained by
a) providing a support
b) providing a metal compound
c) depositing the metal compound on the support
d) optionally calcinating the so obtained catalyst precursor
e) reducing the catalyst precursor, preferably by treatment of the catalyst precursor with a solution of a reducing agent,
f) optionally recovering the catalyst.

In a preferred embodiment of these processes, the catalyst comprises platinum as catalytically active metal. In a preferred embodiment of these processes the support is selected from the group consisting of alpha aluminium oxide ($\alpha$-$Al_2O_3$), beta aluminium oxide ($\beta Al_2O_3$) and gamma aluminium oxide ($\gamma$-$Al_2O_3$). In a preferred embodiment of these processes the oxidant is oxygen and/or hydrogen peroxide.

One embodiment of the invention is directed to a process for the preparation of 3-methyl-2-buten-1-al, wherein 2-methyl-3-buten-2-ol is reacted to 3-methyl-2-buten-1-al in the presence of an oxidant and a catalyst, wherein the catalyst comprises a catalytically active metal, preferably selected from the group consisting of platinum, palladium and gold, and wherein the reaction is conducted at a pH of 7 and wherein a catalyst is used, which comprises the catalytically active metal on a support and wherein the catalytically active metal is mainly located in the outer shell of the catalyst.

One embodiment of the invention is directed to a process for the preparation of 3-methyl-2-buten-1-al, wherein 2-methyl-3-buten-2-ol is reacted to 3-methyl-2-buten-1-al in the presence of an oxidant and a catalyst, wherein the catalyst comprises a catalytically active metal, preferably selected from the group consisting of platinum, palladium and gold, and wherein the reaction is conducted at a pH of 7 and wherein a catalyst is used, which comprises the catalytically active metal on a support and wherein at least 50 weight-%, preferably at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of X from the outer surface of the catalyst, wherein X is 15% of the distance from the outer surface of the catalyst to the center of the catalyst.

One embodiment of the invention is directed to a process for the preparation of 3-methyl-2-buten-1-al, wherein 2-methyl-3-buten-2-ol is reacted to 3-methyl-2-buten-1-al in the presence of an oxidant and a catalyst, wherein the catalyst comprises a catalytically active metal, preferably selected from the group consisting of platinum, palladium and gold, and wherein the reaction is conducted at a pH of 7 and wherein a catalyst is used, which comprises the catalytically active metal on a support and wherein a catalyst is used, which comprises the catalytically active metal on a support and wherein at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of X from the outer surface of the catalyst, wherein X is 30% of the distance from the outer surface of the catalyst to the center of the catalyst.

One embodiment of the invention is directed to a process for the preparation of 3-methyl-2-buten-1-al, wherein 2-methyl-3-buten-2-ol is reacted to 3-methyl-2-buten-1-al in the presence of an oxidant and a catalyst, wherein the catalyst comprises a catalytically active metal, preferably selected from the group consisting of platinum, palladium and gold, and wherein the reaction is conducted at a pH of 7 and wherein a catalyst is used, which comprises the catalytically active metal on a support and wherein at least 50 weight-%, preferably at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of 100 µm from the outer surface of the catalyst.

One embodiment of the invention is directed to a process for the preparation of 3-methyl-2-buten-1-al, wherein 2-methyl-3-buten-2-ol is reacted to 3-methyl-2-buten-1-al in the presence of an oxidant and a catalyst, wherein the catalyst comprises a catalytically active metal, preferably selected from the group consisting of platinum, palladium and gold, and wherein the reaction is conducted at a pH of 7 and wherein a catalyst is used, which comprises the catalytically active metal on a support and wherein at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of 400 µm, preferably to a depth of 300 µm, preferably to a depth of 200 µm from the outer surface of the catalyst.

In a preferred embodiment of these processes, the catalyst comprises platinum as catalytically active metal. In a preferred embodiment of these processes the support is selected from the group consisting of alpha aluminium oxide ($\alpha$-$Al_2O_3$), beta aluminium oxide ($\beta Al_2O_3$) and gamma aluminium oxide ($\gamma$-$Al_2O_3$). In a preferred embodiment of these processes the oxidant is oxygen and/or hydrogen peroxide.

Process Mode

The embodiments of the process mode described hereinafter can suitably be applied in all processes described above.

The pH of the process can be adjusted by any means known to a person skilled in the art, for example by amount and choice of acid(s) added to the process or by the amount of strongly acidic cation exchanger loaded to the reactor.

The process according to the invention can be performed in reaction vessels customary for such reactions, the reaction being configurable in a continuous, semi-batch or batchwise mode. In general, the particular reactions will be performed under atmospheric pressure. The process may, however, also be performed under reduced or increased pressure.

The process according to the invention can be performed under pressure, preferably under a pressure between above 1 bar and 15 bar (absolute), preferably between above 1 bar and 10 bar (absolute).

In case oxygen is used as the oxidant, the process according to the invention can be performed at a partial pressure of oxygen from 0.1 to 15 bar, preferably from 0.2 to 10 bar, preferably from 0.2 to 8 bar, more preferably from 0.2 to 5 bar, more preferably from 1 to 3, preferably from 1 to 2.5, more preferably from 1.2 to 2 bar.

In a preferred embodiment of the invention the process is conducted as a batch process. In a preferred embodiment of the invention the process is conducted as a semi-batch process. In a preferred embodiment of the invention the process is conducted as a continuous process.

In a preferred embodiment of the invention the process is conducted with a fixed-bed catalyst. In case the process according to the invention is conducted with a fixed-bed catalyst, suitable fixed-bed reactors can be selected from the group consisting of trickle-bed reactors, bubble-packed reactors, multi-tubular reactors and plate reactors.

The process according to the invention can be conducted in one fixed-bed reactor or can preferably be conducted in more than one, preferably more than two, more preferably more than three, preferably three to five fixed-bed reactors. The one or more fixed-bed reactors can be arranged in series or in parallel.

The process according to the invention can be conducted at common values of weight hourly space velocity (WHSV), defined as the hourly mass flow of the process feed (in kg/h) per catalyst (in kg). The process can for example be performed at WHSV values of 1 to 20000, preferably 10 to 10000, preferably 20 to 5000, preferably 20 to 500, more preferably from 50 to 100 kg/kg/h.

The process according to the invention can be conducted in one or more fixed-bed reactor(s) with or without heat exchange. In one embodiment of the invention, the fixed-bed reactor(s) can be operated so that a constant temperature is held over one, some or all fixed-bed reactors. In one embodiment of the invention, the fixed-bed reactor(s) can be operated so that a defined temperature gradient is maintained over one, some or all fixed-bed reactors without heat addition or removal. In one embodiment of the invention, the fixed-bed reactor(s) can be operated with a temperature controlled profile, wherein a defined temperature profile is maintained over one, some or all fixed-bed reactors with internal or external heat addition or removal.

In a preferred embodiment of the invention the process is conducted in a trickle-bed reactor with a fixed-bed catalyst. In one embodiment of the invention, the process is conducted with more than one, preferably more than two, more preferably more than three trickle-bed reactors, which are arranged in series or in parallel, preferably in series. In one embodiment, the process is conducted with three to five trickle-bed reactors, which are arranged in series. In one embodiment, one or more, preferably each of the trickle-bed reactors can be provided with a liquid recycle stream.

In a preferred embodiment of the trickle-bed reactor, the components of the reaction can be inserted to the reactor concurrently, meaning that the liquid phase(s) and the gas phase comprising the oxidant oxygen, are inserted to the reactor at the same side, preferably at the top of the reactor.

In one embodiment of the invention the process is conducted in a bubble-packed reactor with a fixed-bed catalyst.

In one embodiment of the invention, the process is conducted with more than one, preferably more than two, more preferably more than three bubble-packed reactors, which are arranged in series or in parallel, preferably in series. In one embodiment, the process is conducted with three to five bubble-packed reactors, which are arranged in series.

In one embodiment of the bubble-packed reactor, the components of the reaction can be inserted in the reactor concurrently, meaning that the liquid phase(s) and the gas phase comprising the oxidant oxygen, are inserted to the reactor at the same side, preferably at the bottom of the reactor. In one embodiment of the bubble-packed reactor, the components of the reaction can be inserted in the reactor countercurrently, meaning that the liquid phase(s) and the gas phase comprising the oxidant oxygen, are inserted to the reactor at opposite sides. In one embodiment, the liquid phase(s) are inserted to the reactor at the bottom of the reactor, whereas the gas phase comprising oxygen as oxidant is inserted at the top of the reactor. In one embodiment, the liquid phase(s) are inserted to the reactor at the top of the reactor, whereas the gas phase comprising oxygen as oxidant is inserted at the bottom of the reactor.

In a preferred embodiment of the invention the process is conducted as a slurry process. The process can be conducted in a slurry-based system as stirred tank reactor or slurry bubble column.

The reaction can be carried out by contacting 2-methyl-3-buten-2-ol, water, acid(s), catalyst, the oxidant and further components, such as for example one or more solvent(s), under suitable reaction conditions.

These components can in principle be contacted with one another in any desired sequence. For example, 2-methyl-3-buten-2-ol, if appropriate dissolved in water or a solvent or in dispersed form, can be initially charged and admixed with the catalyst or, conversely, the catalytic system can be initially charged and admixed with 2-methyl-3-buten-2-ol and water. Alternatively, these components can also be added simultaneously to the reaction vessel.

As an example for a batch-wise slurry process a stirred tank reactor can be used where the catalyst, the reactant, water, acid(s), the oxidant and optionally solvent are loaded. In case oxygen is used as oxidant, the reactor is then pressurized with oxygen. The reaction is then performed until the desired conversion is achieved.

As an example for a batch-wise slurry process a stirred tank reactor can be used where the catalyst, 2-methyl-3-buten-2-ol, if appropriate dissolved in water or solvent or in dispersed form, water, acid(s), the oxidant and optionally one or more solvent(s) are loaded. In case oxygen is used as oxidant, the reactor is then pressurized with oxygen. The reaction is then performed until the desired conversion is achieved.

As an example for a semi-batch process a stirred tank reactor can be used where the catalyst, 2-methyl-3-buten-2-ol, water, acid(s), the oxidant and optionally solvent are loaded. In case oxygen is used as an oxidant, the oxygen is then continuously fed to the reactor until the desired conversion is achieved. As another example for a semi-batch process a fixed bed catalyst in a trickle-bed reactor can be used. The solution of 2-methyl-3-buten-2-ol, water, acid(s), the oxidant, optionally comprising solvent, are then pumped in a loop over the catalyst. In case oxygen is used as oxidant, oxygen is passed as a continuous stream through the reactor. In one embodiment of the invention the oxygen can be added in excess, the excess being released to the off gas, alternatively the oxygen can be added in an amount required to replenish the consumed oxygen.

As an example for a continuous slurry process, a continuous stirred tank reactor can be used in which the catalyst is present. The solution of 2-methyl-3-buten-2-ol, water, acid(s), optionally comprising solvent and the oxidant are added continuously. In case oxygen is used as oxidant, it can be added in excess, off-gas can then be taken out continuously. In an alternative embodiment, oxygen can be added in an amount to replenish the consumed oxygen. The liquid reaction product can be taken off continuously through a filter in order to keep the catalyst in the reactor.

In a further example for a continuous fixed bed process, both the solution of 2-methyl-3-buten-2-ol and the oxidant are continuously fed to a trickle bed reactor containing the catalyst. In this case, it is possible to partly or fully recycle the gas (in case oxygen is used as oxidant) and/or the liquid back to the reactor in order to achieve the desired conversion of reactant(s) and/or oxygen (in case oxygen is used as oxidant).

In a preferred embodiment, the process according to the invention is carried out in a continuous mode.

It has surprisingly been found that the process of the invention leads to selectivities of 3-methyl-2-buten-1-al in the range of over 90%, preferably over 93%, preferably over 95%, preferably over 97% more preferably over 99%.

Preferably the process according to the invention is conducted until a conversion of 2-methyl-3-buten-2-ol in the range of 10 to 99.99%, preferably in the range of 30 to 95%, and most preferably in the range of 50 to 80% is obtained.

Preferably the process according to the invention is performed at a temperature in the range from 1 to 250° C., preferably in the range from 5 to 150° C., preferably in the range from 20 to 100° C., in the range from 20° C. to 70° C., more preferably in the range from 25° C. to 80° C., preferably in the range from 30 to 70° C. and more preferably in the range of 35 to 50° C. In one embodiment of the invention, the process is performed at a temperature in the range of 40 to 80° C.

The obtained crude product may be subjected to conventional purification measures, including distillation or chromatography or combined measures. Suitable distillation devices for the purification of the product include, for example, distillation columns, such as tray columns optionally equipped with bubble cap trays, sieve plates, sieve trays, packages or filler materials, or spinning band columns, such as thin film evaporators, falling film evaporators, forced circulation evaporators, wiped-film (Sambay) evaporators, etc. and combinations thereof.

The invention is further illustrated by the following non-limiting examples:

EXAMPLES—CATALYST PREPARATION

Example C1

Step a): Support: 50 g of aluminium oxide (gamma-$Al_2O_3$ strands with a mean diameter of 1.5 mm (commercially available from Exacer s.r.l. Italy), was heated to 550° C. for 4 hours and maintained at 550° C. for 1 hour.

Step b): 6.68 g of a 15.4 wt. % $Pt(NO_3)_2$ solution in 10 weight % nitric acid and 1.29 g of $Bi(NO_3)_3$ were added to 95.21 g water at room temperature.

Step c): A flask was equipped with 50 g of aluminium oxide obtained in step a) and immersed with the Pt/Bi solution obtained in step b) and stirred for 0.5 hours at 70 mbar while the mixture was heated to 80° C. At 80° C. the solvent was removed within 30 minutes.

Drying was performed in a rotary evaporator for 60 minutes at 80° C.

Step d): The so obtained catalyst precursor was placed in a muffle furnace and heated to 450° C. over a time period of 5 hours. The temperature of 450° C. was maintained for 1 hour.

Step e): Reduction of the catalyst precursor was performed by treatment of the catalyst precursor with a solution of a reducing agent. 50 g of the catalyst precursor obtained in step d) were added to 400 g of water and heated to 60° C. An aqueous sodium formate solution was prepared (34.87 g of sodium formate (97%) plus 88.38 g water) and added dropwise to the catalyst precursor over a time period of 10 minutes. The reaction mixture was maintained at 60° C. for 140 minutes and then left to cool to room temperature under $N_2$.

The catalyst was recovered by filtration and washed with water to a conductivity below 170 µS/cm and subsequently dried at 80° C. for 4 hours.

The so obtained catalyst displayed a Pt content of 1.4 weight % and a molar ratio of Pt:Bi of 1:0.5. The distribution of the catalytically active metal Pt was determined with SEM-EDXS in a cross section of the strands: the majority of the Pt was located within 100 µm from the outer surface of the catalyst.

Example C2

Example C1 was repeated, with the following modification of step c):

Step c): A flask was equipped with 50 g of aluminium oxide obtained in step a) and immersed with the Pt/Bi solution obtained in step b) and stirred for 10 minutes at 70 mbar. The catalyst precursor was recovered by filtration.

The so obtained catalyst displayed a Pt content of 1.4 weight % and a molar ratio of Pt:Bi of 1:0.5. The distribution of the catalytically active metal Pt was determined with SEM-EDXS in a cross section of the strands: the majority of the Pt was located within 100 µm from the outer surface of the catalyst.

Example C3

Step a): Support: 50 g of aluminium oxide (gamma $Al_2O_3$ strands with a diameter of 1.5 mm (commercially available from Exacer s.r.l. Italy) was heated to 550° C. for 4 hours and maintained at 550° C. for 1 hour.

Step b): 6.63 g of a 15.4 weight % $Pt(NO_3)_2$ solution in 10 weight % nitric acid and 5.09 g of $Bi(NO_3)_3$ were added to 29.6 g water at room temperature.

Step c): A flask was equipped with 50 g of aluminium oxide obtained in step a) and rotated at 70 mbar. The Pt/Bi solution obtained in step b) was added via a dropping funnel to the injection nozzle and sprayed onto the support. The deposition step was conducted under mixing for 30 minutes at room temperature. Drying was performed in the rotary evaporator for 60 minutes at 80° C.

Step d): The so obtained catalyst precursor was placed in a muffle furnace and heated to 450° C. over a time period of 5 hours. The temperature of 450° C. was maintained for 1 hour.

Step e): Reduction of the catalyst precursor was performed by treatment of the catalyst precursor with a solution of a reducing agent. 50 g of the catalyst precursor were added to 400 g of water and heated to 60° C. An aqueous sodium formate solution was prepared (34.87 g of sodium formate (97%) plus 88.38 g water) and added dropwise to the catalyst precursor over a time period of 15 minutes. The reaction mixture was maintained at 60° C. for 120 minutes and then left to cool to room temperature under $N_2$.

The catalyst was recovered by filtration and washed with water to a conductivity below 170 µS/cm and subsequently dried at 80° C. for 4 hours.

The so obtained catalyst displayed a Pt content of 1.6 weight % and a molar ratio of Pt:Bi of 1:2. The distribution of the catalytically active metal Pt was determined with SEM-EDXS in a cross section of the strands: the majority of the Pt was located within 100 µm from the outer surface of the catalyst.

Example C4

Example C3 was repeated, with the following modification in step b): 2.55 g (instead of 5.09 g) of $Bi(NO_3)_3$ were added to the solution.

The so obtained catalyst displayed a Pt content of 1.6 weight % and a molar ratio of Pt:Bi of 1:1.

The distribution of the catalytically active metal Pt was determined with SEM-EDXS in a cross section of the strands: the majority of the Pt was located within 100 µm from the outer surface of the catalyst.

Example C5

Example C3 was repeated, with the following modification in step b): 1.27 g (instead of 5.09 g) of $Bi(NO_3)_3$ were added to the solution.

The so obtained catalyst displayed a Pt content of 1.6 weight % and a molar ratio of Pt:Bi of 1:0.5. The distribution of the catalytically active metal Pt was determined with SEM-EDXS in a cross section of the strands: the majority of the Pt was located within 400 µm from the outer surface of the catalyst.

Example C6

Step a): 40 g of gamma-aluminium oxide (strands with a diameter of 1.5 mm) was heated to 550° C. for 4 hours and maintained at 550° C. for 1 hour.

Step b): A 15.7 wt. % $Pt(NO_3)_2$ solution in 10 weight % nitric acid was prepared.

Step c): A rotary plate was equipped with 40 g of aluminium oxide obtained in step a), rotated and heated to 100° C. 15.95 g of a 15.7 wt. % $Pt(NO_3)_2$ solution in 10 weight % nitric acid was sprayed onto the support with an injection nozzle within 1 hour and 6 minutes. After the addition was complete the mixture was rotated for an additional 10 minutes on the hot rotary plate and subsequently dried.

Step d): The so obtained catalyst precursor was placed in a muffle furnace and heated to 450° C. over a time period of 3 hours. The temperature of 450° C. was maintained for 1 hour.

Step e): Reduction of the catalyst precursor was performed by treatment of the catalyst precursor with a solution of a reducing agent. 41.97 g of the catalyst precursor was added to 399.94 g of water and heated to 60° C. An aqueous sodium formate solution was prepared (29.32 g of sodium formate plus 74.13 g water) and added dropwise to the catalyst precursor over a time period of 15 minutes. The reaction mixture was maintained at 60° C. for 120 minutes and then left to cool to room temperature under $N_2$.

The catalyst was recovered by filtration and washed with water to a conductivity below 132.5 µS/cm and subsequently dried at 80° C. for 4.5 hours.

The so obtained catalyst displayed Pt content of 2.6 weight %. The distribution of the catalytically active metal Pt was determined with SEM-EDXS in a cross section of the strands: the majority of the Pt was located within 100 µm from the surface of the catalyst.

Figure 1:
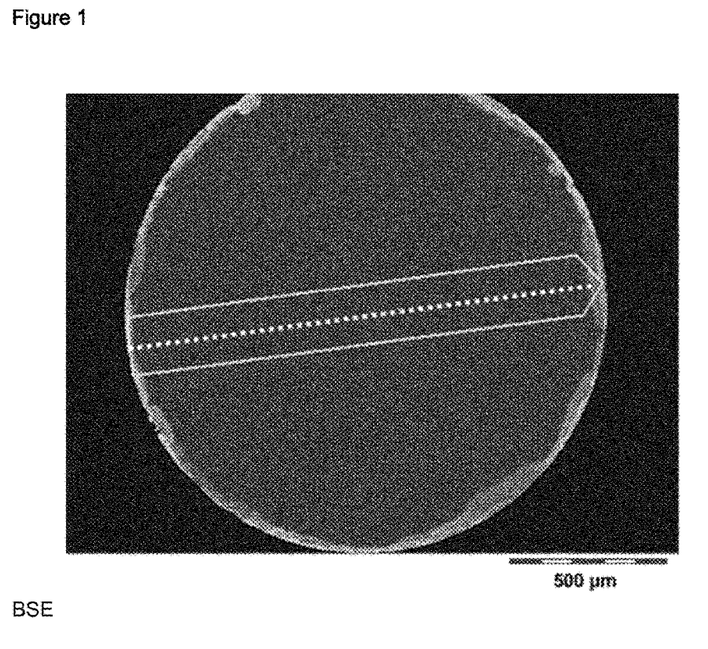
FIGS. 1 and 2 display the Pt distribution in the catalyst of example C6.
Figure 2:
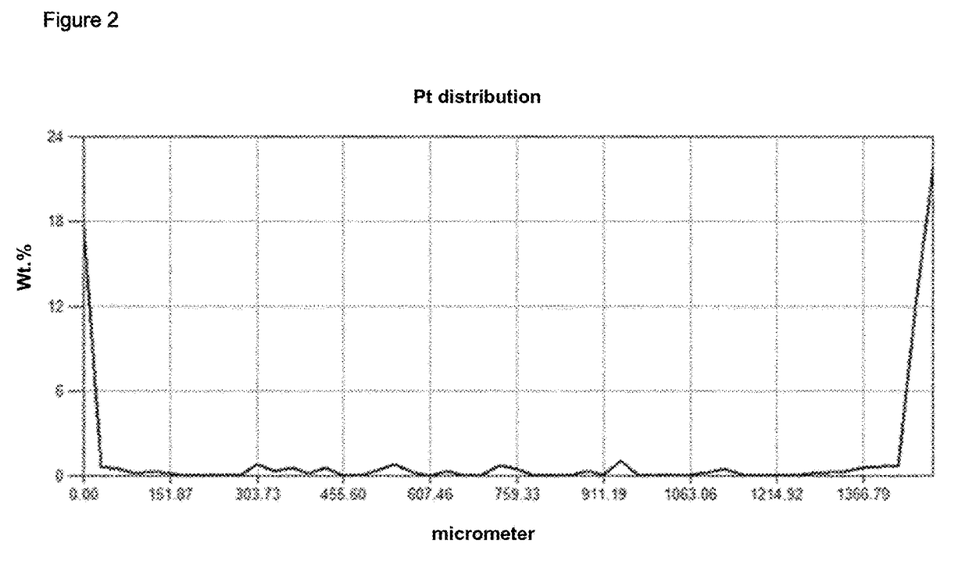

FIGS. 1 and 2 display the Pt distribution in the catalyst of example C6. In FIG. 2 the Y-axis shows the local Pt-concentration in weight % measured by EDX, while the X-axis shows the position at which the measurement was taken. The distances are taken along the dotted line in the upper picture and the zero point is at the left side.

Example C7

C7A—IMC preparation (step g)/PtBi was synthesized as follows (steps g-1 to g-3):

1.2 mmol $PtCl_4$ and 1.2 mmol $BiCl_3$ were weighed out in an argon-filled glove box and dissolved in 10 mL of THF by stirring. The reducing agent potassium triethylborohydride $KBH(C_2H_5)_3$ (1.0 M in THF, Sigma-Aldrich) with 30 mol % excess was mixed with THF to form a 15 mL solution. Then the solution was drawn up into a syringe and injected into a solution of the reducing agent under vigorous stirring. The sample was dried under vacuum until most of the THF was gone. Hexane was then added to precipitate the PtBi—KCl powders. The sample was then washed three times with THF and hexane without contacting air. The product was then dried under vacuum for 2 h and transferred to the glove box. The product was placed into silica tubes, which were sealed under vacuum and then annealed at 400° C. for 6 h. The resulting PtBi—KCl powders were analyzed with PXRD as described below. P-XRD analysis confirmed the IMC structure.

The KCl containing powders were then mixed with water and centrifuged until the solution did not contain any chloride ($AgNO_3$ test of the wash solution). PVP was then added and the solution was ultrasonicated.

C7B—Preparation of a Supported IMC Catalyst

Step a): Support: 8.25 g of aluminium oxide (gamma-$Al_2O_3$ strands with a mean diameter of 1.5 mm (commercially available from Exacer s.r.l. Italy), was heated to 550° C. for 4 hours and maintained at 550° C. for 1 hour.

Step c): 6.19 g of an aqueous suspension obtained in example C7A comprising 0,165 g of the PtBi IMC and 0,017 g PVP were ultrasonicated for 10 minutes. The suspension was then added to 8.25 g of the support and mixed with a spatula for approx. 15 minutes. The catalyst was subsequently dried at 80° C. for 1 hour.

The distribution of the catalytically active metal Pt was determined with SEM-EDXS in a cross section of the strands: the majority of the Pt was located within 100 µm from the outer surface of the catalyst. The resulting catalyst was examined with XPS as described below. The XPS analysis confirmed the IMC structure.

Example C8

C8A—IMC preparation (step g)/$Pt_2Bi_3$ was synthesized as follows (steps g-1 to g-3):

0.6 mmol $PtCl_4$ and 0.9 mmol $BiCl_3$ were weighed out in an argon-filled glove box and dissolved in 10 mL of THF by stirring. The reducing agent potassium triethylborohydride $KBH(C_2H_5)_3$ (1.0 M in THF, Sigma-Aldrich) with 30 mol % excess was mixed with THF to form a 15 mL solution. Then the solution was drawn up into a syringe and injected into a solution of the reducing agent under vigorous stirring. The sample was dried under vacuum until most of the THF was gone. Hexane was then added to precipitate the $Pt_2Bi_3$—KCl powders. The sample was then washed three times with THF and hexane without contacting air. The product was then dried under vacuum for 2 h and transferred to the glove box. The product was placed into silica tubes, which were sealed under vacuum and then annealed at 400° C. for 6 h. The resulting $Pt_2Bi_3$—KCl powders were analyzed with PXRD as described below. P-XRD analysis confirmed the IMC structure.

The KCl containing powders were then mixed with water and centrifuged until the solution did not contain any chloride ($AgNO_3$ test of the wash solution). PVP was then added and the solution was ultrasonicated.

C8B—Preparation of a Supported IMC Catalyst

Step a): Support: 12.9 g of aluminium oxide (gamma-$Al_2O_3$ strands with a mean diameter of 1.5 mm (commercially available from Exacer s.r.l. Italy), was heated to 550° C. for 4 hours and maintained at 550° C. for 1 hour.

Step c): 9.6 g of an aqueous suspension obtained in example C8A comprising 0,258 g of the $Pt_2Bi_3$ IMC and 0,026 g PVP were ultrasonicated for 10 minutes. The suspension was then added to 12.9 of the support and the support was spray impregnated at 500 mbar for 15 minutes in a rotary evaporator. The catalyst was subsequently dried at 80° C. for 1 hour.

The distribution of the catalytically active metal Pt was determined with SEM-EDXS in a cross section of the strands: the majority of the Pt was located within 100 μm from the outer surface of the catalyst. The resulting catalyst was examined with XPS as described below. The XPS analysis confirmed the IMC structure.

Example C9

C9A—IMC preparation (step g)/$PtBi_2$ was synthesized as follows (steps g-1 to g-3):

1.2 mmol $PtCl_4$ and 2.4 mmol $BiCl_3$ were weighed out in an argon-filled glove box and dissolved in 10 mL of THF by stirring. The reducing agent potassium triethylborohydride $KBH(C_2H_5)_3$ (1.0 M in THF, Sigma-Aldrich) with 30 mol % excess was mixed with THF to form a 15 mL solution. Then the solution was drawn up into a syringe and injected into a solution of the reducing agent under vigorous stirring. The sample was dried under vacuum until most of the THF was gone. Hexane was then added to precipitate the $PtBi_2$—KCl powders. The sample was then washed three times with THF and hexane without contacting air. The product was then dried under vacuum for 2 h and transferred to the glove box. The product was placed into silica tubes, which were sealed under vacuum and then annealed at 400° C. for 6 h. The resulting $PtBi_2$—KCl powders were analyzed with P-XRD as described below. P-XRD analysis confirmed the IMC structure.

The KCl containing powders were then mixed with water and centrifuged until the solution did not contain any chloride ($AgNO_3$ test of the wash solution). PVP was then added and the solution was ultrasonicated.

C9B—Preparation of a Supported IMC Catalyst

Step a): Support: 14.65 g of aluminium oxide (gamma-$Al_2O_3$ strands with a mean diameter of 1.5 mm (commercially available from Exacer s.r.l. Italy), was heated to 550° C. for 4 hours and maintained at 550° C. for 1 hour.

Step c): 10.99 g of an aqueous suspension obtained in example C9A comprising 0,293 g of the $PtBi_2$ IMC and 0,029 g PVP were ultrasonicated for 10 minutes. The suspension was then added to 14.65 g of the support and the support was impregnated at 500 mbar for 15 minutes in a rotary evaporator. The catalyst was subsequently dried at 80° C. for 1 hour.

The distribution of the catalytically active metal Pt was determined with SEM-EDXS in a cross section of the strands: the majority of the Pt was located within 100 μm from the outer surface of the catalyst. The resulting catalyst was examined with XPS as described below. The XPS analysis confirmed the IMC structure.

PXRD Analysis

The Pt—Bi materials were analyzed regarding their phase purity and structure with XRD using a Bruker D8 Advance diffractometer from Bruker AXS GmbH, Karlsruhe equipped with a Lynxeye XE 1D-Detector, using variable slits, from 10° to 90° 2theta. The anode of the X-ray tube consisted of copper. To suppress the Cu radiation, a nickel filter was used. The following parameters were used: Voltage: 40 kV, Current: 40 mA, Step size: 0.02° 2theta, Scan speed 0.2 s/step, Soller slits (primary side): 2.5°; Soller slits (secondary side): 2.50; Divergence slit: 0.17°.

The phases present in each sample were identified by search and match of the data available from International Centre for Diffraction Data (ICDD, Version 2015).

XPS Analysis

XPS analysis was performed with a Phi Versa Probe 5000 spectrometer using monochromatic Al Kα radiation (50.4 W) with a spot size of 200×200 μm in standard configuration. The instrument work function was calibrated to give a binding energy (BE) of 84.00 eV for the Au 4f7/2 line of metallic gold and the spectrometer dispersion was adjusted to give a BE of 932.62 eV for the Cu 2p3/2 line of metallic copper. The built in Phi charge neutralizer system was used on all specimens. To minimize the effects of differential charging, all samples were mounted insulated against ground. Survey scan analyses were carried out with a pass energy of 117.4 eV and an energy step size of 0.5 eV. High resolution analyses were carried out on the same analysis area with a pass energy of 23.5 eV and an energy step size of 0.1 eV. Spectra have been charge corrected to the main line of the carbon 1s spectrum set to 284.8 eV as a typical value quoted for the energy of the peak of adventitious hydrocarbon. All Spectra were analyzed using CasaXPS software version 2.3.20 using Shirley background subtraction. Relative sensitivity factors and transmission function as provided by the instrument manufacturer were used for quantification.

EXAMPLES—PROCESS

Gas Chromatographic Analysis:
GC-system and separation method:
GC-system: Agilent 7890A
GC-Column: RTX-200 (60 m (Length), 0.32 mm (ID), 1.0 μm (Film))
Temperature program: 10 minutes at 60° C., 60° C. to 280° C. in 6° C./min, 10 minutes at 280° C.

Example 1

A 0.27 L metal autoclave was charged with 4 g 2-methyl-3-buten-2-ol (DMVC, dimethylvinylcarbinol, obtained from BASF), 76 g of demineralized water and 0.9 g platinum on aluminium oxide (5 w/w.-% Pt on $Al_2O_3$, obtained from Strem (ESCAT 2941), corresponds to 0.5 mol-% platinum based on DMVC). Finally, 4 drops of $H_3PO_4$ (85 w/w.-%)

were added to the reactor and the solution was stirred at 1000 rpm and heated to 70° C. $O_2$ (5.9 l/h) was metered to the reactor for 6.5 hours under 2 bar constant $O_2$ pressure at such a rate that the pressure remains constant (no off-gas). At the end of the reaction the autoclave was cooled down to room temperature and depressurized before opening. The reaction mixture was then filtered to remove the catalyst and the filtrate was analyzed by gas chromatography with an FID detector and showed to contain 55 area-% of unconverted 2-methyl-3-buten-2-ol (DMVC), 7 area-% of 3-methyl-2-buten-1-ol (prenol), 36 area-% 3-methyl-2-buten-1-al (prenal) and 1 area-% 3,3-dimethylacrylic acid. This corresponds to a conversion of DMVC plus prenol of 37.8% and a selectivity to prenal of 97.7%.

The invention claimed is:

1. A process for the preparation of 3-methyl-2-buten-1-al, wherein 2-methyl-3-buten-2-ol is reacted to 3-methyl-2-buten-1-al in the presence of an oxidant and a catalyst, wherein the catalyst comprises a catalytically active metal and wherein the reaction is conducted at a pH of below 7.

2. The process according to claim 1, wherein the reaction is performed at a pH of ≤6.

3. The process according to claim 1, wherein the catalytically active metal is selected from the group consisting of platinum, palladium and gold.

4. The process according to claim 2, wherein the catalytically active metal is selected from the group consisting of platinum, palladium and gold.

5. The process according to claim 1, wherein the reaction is performed in the presence of a catalyst, wherein the catalytically active material is on a support.

6. The process according to claim 4, wherein the reaction is performed in the presence of a catalyst, wherein the catalytically active material is on a support.

7. The process according to claim 1, wherein the support is selected from the group consisting of carbonaceous and oxidic materials.

8. The process according to claim 6, wherein the support is selected from the group consisting of carbonaceous and oxidic materials.

9. The process according to claim 1, wherein the oxidant is selected from the group consisting of oxygen and hydrogen peroxide.

10. The process according to claim 8, wherein the oxidant is selected from the group consisting of oxygen and hydrogen peroxide.

11. The process according to claim 1, wherein the reaction is performed at a temperature of 20° C. to 100° C.

12. The process according to claim 10, wherein the reaction is performed at a temperature of 20° C. to 100° C.

13. A process for the preparation of 3-methyl-2-buten-1-al, wherein 2-methyl-3-buten-2-ol is reacted to 3-methyl-2-buten-1-al in the presence of an oxidant and a catalyst, wherein the catalyst comprises a catalytically active metal and wherein the reaction is conducted at a pH of ≤7, wherein the reaction is performed in the presence of a liquid phase, which contains at least 25 weight-% of water.

14. The process according to claim 12, wherein the reaction is performed in the presence of a liquid phase, which contains at least 25 weight-% of water.

15. The process according to claim 1, wherein the reaction is performed under a partial pressure of oxygen between 0.2 and 8 bar.

16. The process according to claim 14, wherein the reaction is performed under a partial pressure of oxygen between 0.2 and 8 bar.

17. The process according to claim 1, wherein the reaction is performed in the presence of a liquid phase, which contains at least 25 weight-% of water.

* * * * *